(12) United States Patent
Itou et al.

(10) Patent No.: US 8,066,633 B2
(45) Date of Patent: Nov. 29, 2011

(54) ELECTRIC BENDING ENDOSCOPE DEVICE

(75) Inventors: Seigo Itou, Hachioji (JP); Masanobu Koitabashi, Hachioji (JP)

(73) Assignee: Olympus Medical Systems Corp., Tokyo (JP)

(*) Notice: Subject to any disclaimer, the term of this patent is extended or adjusted under 35 U.S.C. 154(b) by 664 days.

(21) Appl. No.: 12/168,358

(22) Filed: Jul. 7, 2008

(65) Prior Publication Data

US 2008/0262311 A1    Oct. 23, 2008

Related U.S. Application Data

(63) Continuation of application No. PCT/JP2006/323227, filed on Nov. 21, 2006.

(30) Foreign Application Priority Data

Jan. 13, 2006  (JP) ................. 2006-006785

(51) Int. Cl.
    *A61B 1/00*   (2006.01)
(52) U.S. Cl. ........................................... 600/152
(58) Field of Classification Search .................. 600/101, 600/117, 118, 139, 145, 146, 152
See application file for complete search history.

(56) References Cited

U.S. PATENT DOCUMENTS

| | | | |
|---|---|---|---|
| 5,658,238 A * | 8/1997 | Suzuki et al. | 600/150 |
| 2002/0165432 A1* | 11/2002 | Matsui | 600/145 |
| 2003/0195389 A1 | 10/2003 | Motoki et al. | |
| 2004/0034279 A1 | 2/2004 | Arai et al. | |
| 2004/0054258 A1 | 3/2004 | Maeda et al. | |
| 2004/0267093 A1 | 12/2004 | Miyagi et al. | |

FOREIGN PATENT DOCUMENTS

| | | |
|---|---|---|
| JP | 04-129695 | 4/1992 |
| JP | 06-304126 | 11/1994 |
| JP | 08-224206 | 9/1996 |
| JP | 2003-245246 | 9/2003 |

* cited by examiner

*Primary Examiner* — Anhtuan Nguyen
*Assistant Examiner* — Christopher Sponheimer
(74) *Attorney, Agent, or Firm* — Scully, Scott, Murphy & Presser, P.C.

(57) ABSTRACT

An electric bending endoscope device includes an endoscope with a driving unit, a control unit and an operation portion with a bending instruction portion. The operation portion includes a correction algorithm calculating portion in which the output range of instruction signal of the joystick is converted to coincide with the predetermined output range of the bending instruction portion instruction-signal being the operation signal outputted by the operation portion according to the joystick being the bending instruction portion to be fitted to the operation portion, to generate the bending instruction portion operation-signal.

4 Claims, 19 Drawing Sheets

ROTATE COORDINATE POSITION OF SIGNAL BY ANGLE OF θ

FIG.25
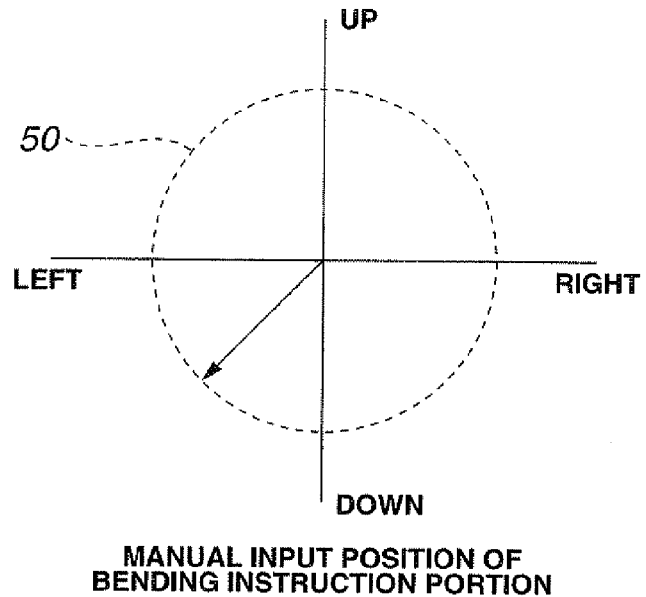
MANUAL INPUT POSITION OF
BENDING INSTRUCTION PORTION
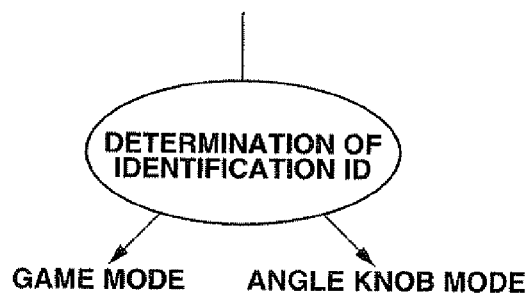
FIG.26
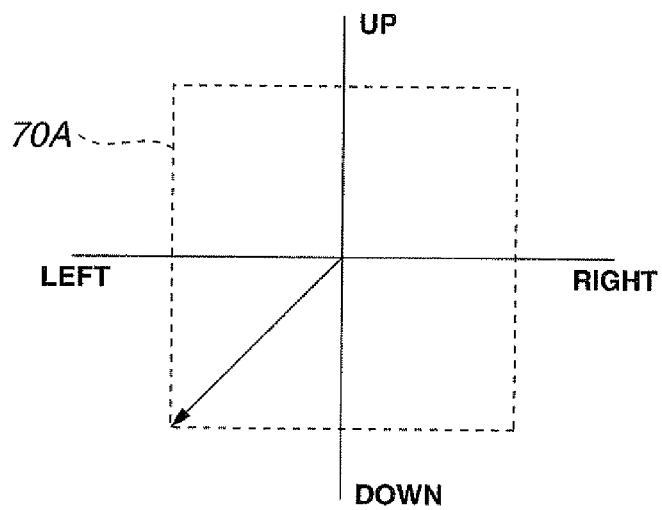
ELECTRIC SIGNAL COORDINATE
AFTER SIGNAL PROCESSING
(GAME MODE)

ELECTRIC BENDING ENDOSCOPE DEVICE

CROSS REFERENCE TO RELATED APPLICATION

This application is a continuation application of PCT/JP2006/323227 filed on Nov. 21, 2006 and claims benefit of Japanese Application No. 2006-006785 filed in Japan on Jan. 13, 2006, the entire contents of which are incorporated herein by this reference.

BACKGROUND OF THE INVENTION

1. Field of the Invention

The present invention relates to an electric bending endoscope device including an operation portion to which a bending instruction portion can be attached and which outputs a bending instruction portion operation-signal and an electric bending endoscope which is electrically bent to a state corresponding to the bending instruction portion operation-signal by operating the bending instruction portion.

2. Description of the Related Art

Heretofore, an endoscope has been widely used. An operator inserting an elongated insertion portion of the endoscope into a body cavity enables observing organs in the body cavity and performing various treatments using a treatment instrument inserted into the channel thereof, if required. A worker in an industrial field inserting an elongated insertion portion of the endoscope enables observing or inspecting damage and corrosion inside a boiler, a turbine, an engine, a chemical plant and the like.

Such an endoscope is provided with a bendable bending portion on the proximal end side of the distal end portion of the elongated insertion portion. In the endoscope, a user such as an operator operates bending instruction portion such as a bending operation knob provided on the operation portion to input a bending direction and a bending angle of the bending portion to bending drive portion for bending the bending portion.

The bending drive portion mechanically pulls or relaxes a bending operation wire connected to a bending piece configuring the bending portion based on a bending direction and a bending angle given by the bending operation knob to bend the bending portion.

In general, the bending drive portion has been operated using man power as a power source, however, in recent years, there is available an electric bending endoscope which pulls or relaxes a bending operation wire using bending drive portion such as a motor to bend the bending portion.

For example, the electric bending endoscope bends the bending portion in such a manner that a motor is electrically rotated and controlled to pull or relax the bending operation wire by the driving force of the motor based on the bending instruction portion operation-signal and the detection signal on bending state of the bending portion outputted by the operation portion so that the instruction state of the bending instruction portion provided on the operation portion coincides with the bending state of the bending portion in an absolute positional relationship (hereinafter referred to as "absolute position control").

As the bending instruction portion, there are available a joystick and a track ball.

For example, in the absolute position control of the joystick, tilting the joystick instructs a bending direction and a bending angle. In other word, the direction in which the joystick is tilted corresponds to the direction in which an operator wants to bend the bending portion and the angle at which the joystick is tilted corresponds to the angle at which the bending portion is bent. For example, when the joystick stands upright, i.e., a tilt angle of the joystick is 0 degrees, the bending portion is in a non-bending state (or, in a straightened state). Due to this, the operator can easily grasp how the bending portion is bent in the body cavity through the operator's sense of the finger holding the joystick.

As a related art of an electric bending endoscope, there has been known arts described in Japanese Patent Application Laid-Open Publication Nos. 2003-245246 and 08-224206, for example.

Japanese Patent Application Laid-Open Publication No. 2003-245246 discloses a technique related to an electric bending endoscope device in which a joystick is provided on the operation portion of an electric bending endoscope to easily perform a positioning work (or, a calibration work) in which the instruction state is caused to coincide with the bending state of the bending portion.

Japanese Patent Application Laid-Open Publication No. 08-224206 discloses a technique related to an electric bending endoscope in which a plurality of bending operation switches such as upper, lower, left and right switches and joysticks is selectively attached to a receiving portion of a bending switch provided on the operation portion to improve user friendliness.

SUMMARY OF THE INVENTION

An electric bending endoscope device according to the present invention includes: an endoscope having a bending portion in its insertion portion to be inserted to a test subject; drive portion for bending the bending portion; operation portion having a bending instruction portion which outputs an instruction signal for instructing the bending movement by inputting instructions of bending movements to the endoscope, generating an operation signal based on the instruction signal from the bending instruction portion and outputting the operation signal; and control unit for controlling the drive portion based on the operation signal from the operation portion; wherein the operation portion, to which the bending instruction portion can be attached, converts the output range of the instruction signal of the bending instruction portion to cause the output range of the instruction signal of the bending instruction portion to coincide with a predetermined output range of the operation signal outputted by the operation portion according to each of the attached bending instruction portions and generates the operation signal.

BRIEF DESCRIPTION OF THE DRAWINGS

FIG. 25 is a diagram for setting the operation mode of the operation portion by determination process based on information from identification ID in FIG. 23;

FIG. 26 is an electric signal coordinate diagram of the bending instruction portion instruction-signal after the signal processing in the game mode;

DETAILED DESCRIPTION OF THE PREFERRED EMBODIMENT(S)

The embodiment of the present invention is described below with reference to the accompanied drawings.

First Embodiment

Figure 1:
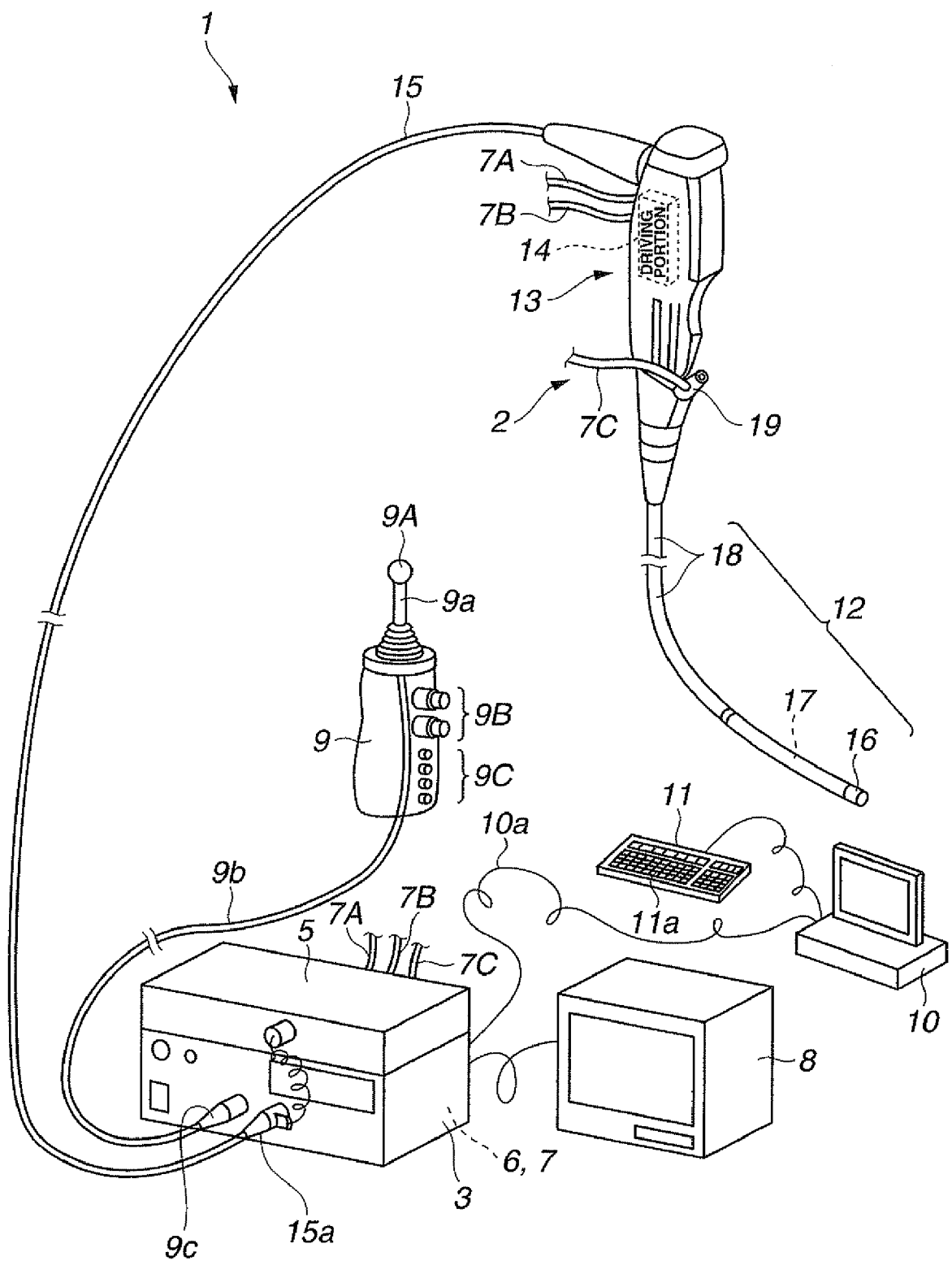
FIG. 1 is a system configuration diagram of an electric bending endoscope device according to a first embodiment of the present invention.
Figure 2:
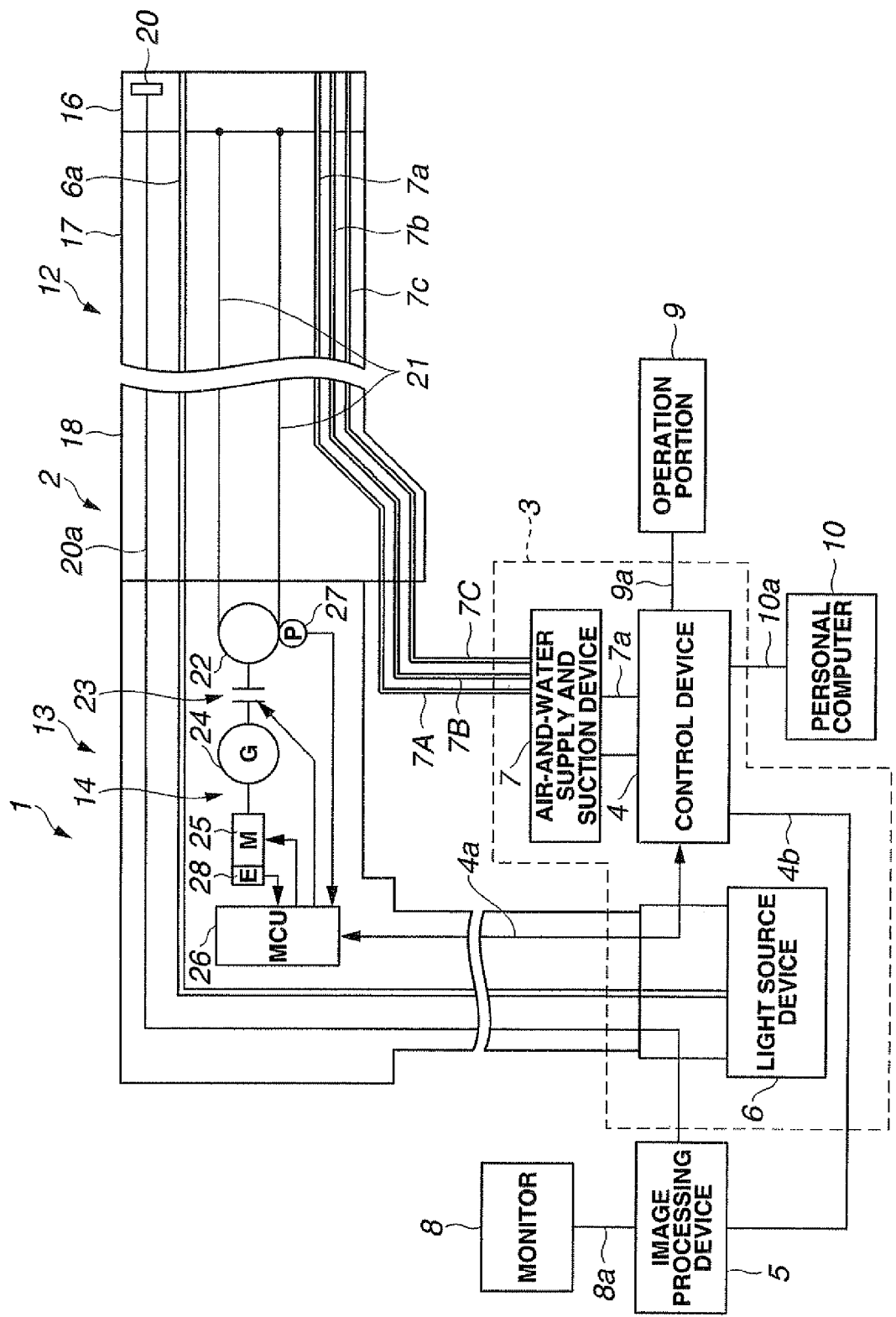
FIG. 2 is a schematic configuration diagram of the electric bending endoscope device in FIG. 1.

FIGS. 1 and 2 describe an electric bending endoscope device according to the first embodiment of the present invention. FIG. 1 is a system configuration diagram of the electric bending endoscope device. FIG. 2 is a schematic configuration diagram of the electric bending endoscope device in FIG. 1.

As illustrated in FIGS. 1 and 2, an electric bending endoscope device 1 of the first embodiment includes an electric bending endoscope (hereinafter abbreviated to "endoscope") 2, a control unit 3, an image processing device 5 for generating a video signal from an image signal transmitted through a signal cable 20a extended from the image pickup device 20 of the endoscope 2, a monitor 8 being a display device for receiving the video signal generated by the image processing device 5 and displaying an endoscope image, an operation portion 9 electrically connected to the control unit 3 and a personal computer (hereinafter abbreviated to "PC") 10 which is electrically connected to the control unit 3 and acts as setting input portion detachable from the control unit 3.

The endoscope 2 incorporates the image pickup device 20, for example, in an distal-end rigid portion 16 forming an endoscope insertion portion (hereinafter abbreviated to "insertion portion") 12 and includes as a driving portion 14 being bending drive portion for bending a bending portion 17 of the insertion portion 12 in its driving unit 13 acting also as a holding portion.

The control unit 3 includes a control device 4 being control means for controlling the driving portion 14 of the endoscope 2 to control the bending operation of the bending portion 17, an undermentioned light source device 6 and air-and-water supply and suction device 7 therein.

The operation portion 9 is capable of outputting to the control unit 3 an operation signal such as a bending instruction portion operation-signal for giving the bending portion 17 instructions about a bending direction and a bending angle and is formed as operation means detachable from the control unit 3.

The endoscope 2 includes an elongated insertion portion 12 to be inserted into a part of an object to be observed, the driving unit 13 which is connected to the proximal end portion of the insertion portion 12 and has the driving portion 14, a universal cord 15 incorporating a signal cable 20a extended from the side of the driving unit 13 and connected to the image pickup device 20 and a light guide fiber 6a for transmitting illumination light from the light source device 6 and a connector portion 15*a* which is provided at the end of universal cord 15 and is a connection portion detachable from the control unit 3.

The insertion portion 12 includes the distal-end rigid portion 16 provided at the distal end thereof, the bendable bending portion 17 provided at the rear portion of the distal-end rigid portion 16 and an elongated soft flexible tube portion 18 coupled to the bending portion 17.

The distal-end rigid portion 16 includes at least an image pickup portion (not shown) having an objective optical system incorporating the image pickup device 20 such as CCD as image pickup portion and a circuit board for driving the image pickup device 20 and an illumination optical system (not shown) supplied with illumination light through the light guide fiber 6*a*.

As illustrated in FIG. 2, the insertion portion 12 includes an air supply pipe 7*a*, a water supply pipe 7*b* and a suction pipe 7*c*, for example. The pipes 7*a*, 7*b* and 7*c* are connected to the air-and-water supply and suction device 7 through an air supply tube 7A, a water supply tube 7B and a suction tube 7C respectively.

Incidentally, the suction tube 7C is connected to a forceps plug 19 (refer to FIG. 1) with a suction tube provided on the endoscope 2. The forceps plug 19 with a suction tube communicates with the suction pipe 7*c* to enable treatment instruments (not shown) such as forceps to be inserted into the pipe.

A bending operation wire 21 extending from the driving unit 13 and bending the bending portion 17 upward and downward and a bending operation wire (not shown) bending the bending portion 17 leftward and rightward are inserted into the insertion portion 12.

The configuration related to the bending operation wire 21 for the upward and the downward operation is described below. The bending operation wire for the leftward and the rightward operation which is the same in configuration as the bending operation wire 21 for the upward and the downward operation is not shown for the simplicity of illustration and omitted in description thereof.

As illustrated in FIG. 2, both ends of the bending operation wire 21 are coupled and fixed to, for example, chains (not shown) which are engaged with a rotatable sprocket 22 for upward and downward operation provided in the driving portion 14. Due to this, the rotation of the sprocket 22 in a predetermined direction pulls the bending operation wire 21 fixed to the chains to bend the bending portion 17 in a predetermined direction.

The sprocket 22 is disposed in, for example, the driving unit 13. The driving force of an upward and downward motor 25 composed of, for example, a DC motor being bending drive portion is transmitted to the sprocket 22 through a plurality of gear trains 24 and a clutch mechanism portion 23 which can disengage the gears of a gear train 24 being engaged with each other.

The amount of rotation of the sprocket 22 is detected by a potentiometer 27. The detection results are supplied to a motor control unit (MCU) 26 provided in the driving portion 14.

The motor 25 is connected to an encoder 28 for detecting the amount of rotation of the motor 25. The detection results of the encoder 28 are supplied to the MCU 26.

The MCU 26 is electrically connected to the control device 4 in the control unit 3 through a signal line 4*a*. The MCU 26 communicates with the control device 4 and outputs the detection results from the potentiometer 27 and the encoder 28 to the control device 4 as a quantity of state detecting signal.

The MCU 26 is supplied with a control signal generated based on the bending instruction portion operation-signal which is the output signal of the undermentioned operation portion 9 through the control device 4. The MCU 26 generates a drive signal based on the supplied control signal and outputs the drive signal to the motor 25 to control the rotation of the motor 25.

As described above, the control unit 3 includes the control device 4, the light source device 6 and the air-and-water supply and suction device 7.

The control device 4 in the control unit 3 is electrically connected to the image processing device 5 through a signal line 4*b*. In addition, the control device 4 in the control unit 3 is electrically connected to the air-and-water supply and suction device 7 in the control unit 3 through a signal line 7*a*. The air-and-water supply and suction device 7 may be integrated with the control device 4.

A connector portion 9*c* of a connection cord 9*b* is connected to the control unit 3. The proximal end side of the connection cord 9*b* is connected to the operation portion 9. The operation portion 9 is electrically connected to the control device 4 in the control unit 3 through the connection cord 9*b*.

The control device 4 generates a control signal for bending the bending portion 17 based on the bending instruction portion operation-signal as an operation signal outputted from the operation portion 9, outputs the control signal to the MCU 26 in the driving unit 13 and controls the bending operation of the bending portion 17.

The control device 4 controls the air-and-water supply and suction device 7 and the image processing device 5 based on the operation signal of the air-and-water supply and suction and the scope switch operation signal outputted from the operation portion 9.

The image processing device 5 generates a video signal from the image signal transmitted through the signal cable 20*a* extended from the image pickup device 20 of the endoscope 2.

The light source device 6 supplies illumination light to the illumination optical system (not shown) in the endoscope 2 through the light guide fiber 6*a*.

The air-and-water supply and suction device 7 is controlled so as to supply air to the air supply pipe 7*a*, water to the water supply pipe 7*b* and suck at the suction pipe 7*c* in the endoscope 2 based on the control signal from the control device 4 generated according to the operation signal (operation signals for the air-and-water supply and suction switch and the scope switch) from the operation portion 9.

The monitor 8 is electrically connected to the image processing device 5 through the signal line 8*a* and displays an endoscope image thereon according to the video signal generated by the image processing device 5 and inputted thereto through the signal line 8*a*.

Information such as the operation signal and the quantity of state detecting signal existing in the control device 4 may be transmitted to the image processing device 5 through the signal line 4*b*, and, after being subjected to a displaying process by the image processing device 5, may be outputted through the signal line 8*a* and displayed on the monitor 8 along with the endoscope image.

The PC 10 is electrically and detachably connected to the control device 4 through the signal line 10*a*. The PC 10 is used to input various setting values required, for example, to bend the bending portion 17 to a recording portion (not shown) in the control device 4 or change the various setting values by key operation using keys 11*a* of a keyboard 11.

Although the present embodiment describes the configuration in which the PC 10 is connected to the control unit 3, the PC 10 may be connected to the control unit 3, only if needed.

Figure 3:
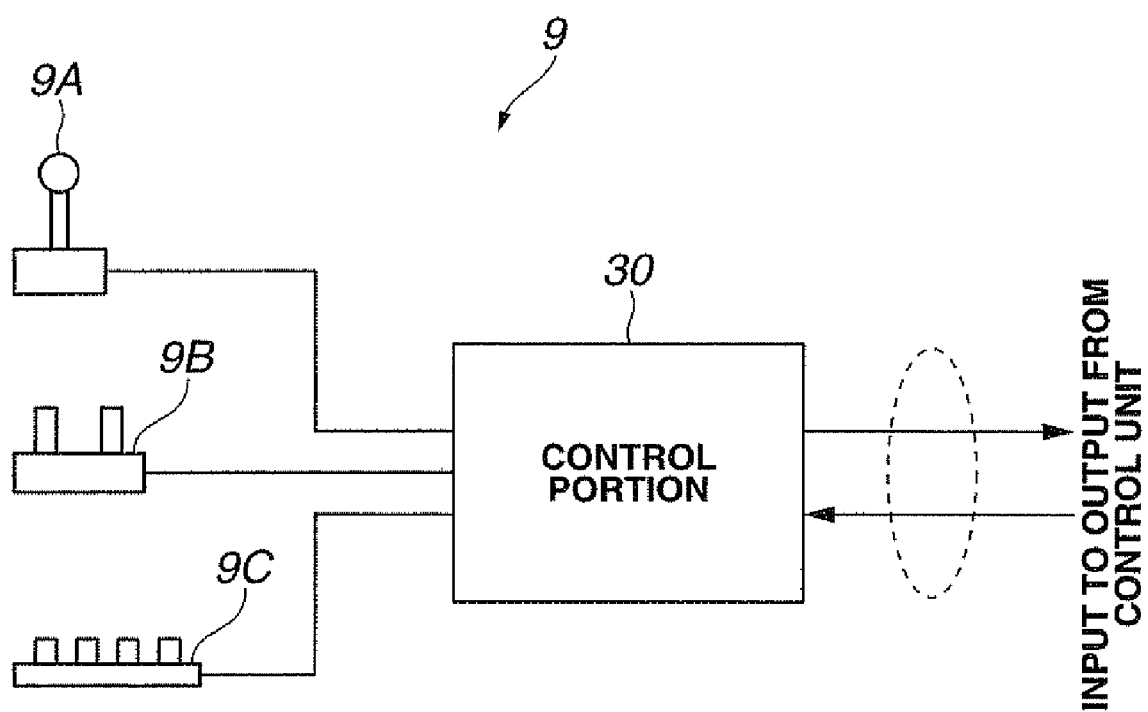
FIG. 3 is a schematic configuration diagram of the operation portion illustrated in FIG. 1.
Figure 4:
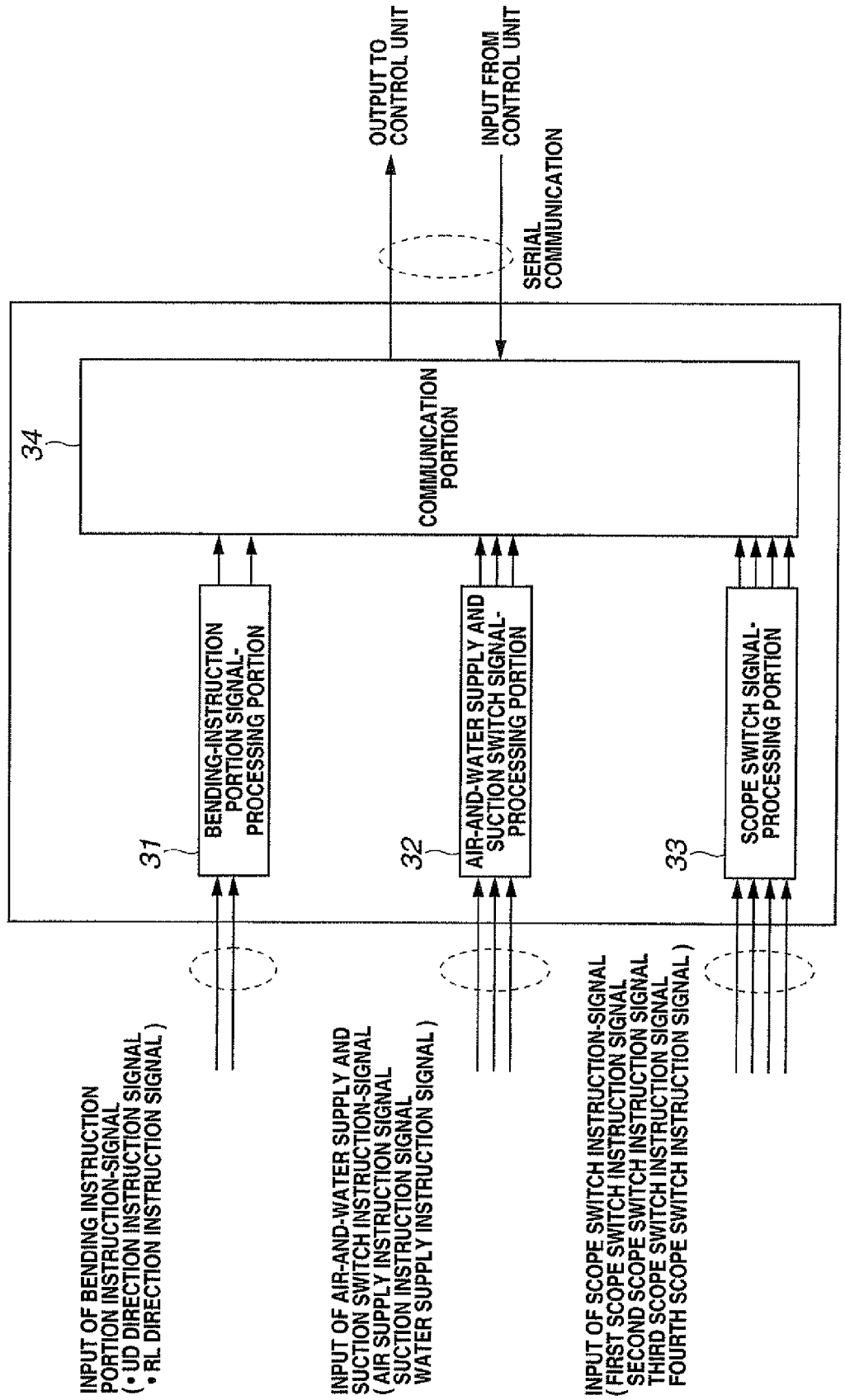
FIG. 4 is a block diagram illustrating the configuration of the control portion in FIG. 3.
Figure 5:
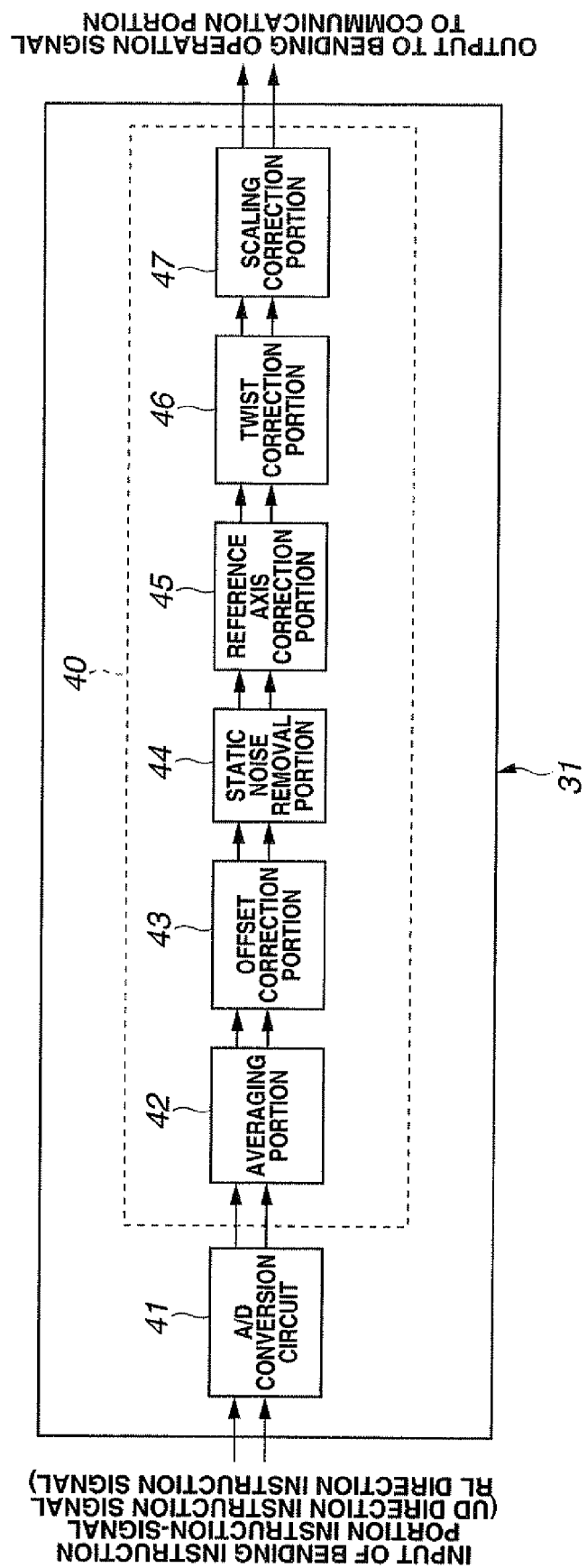
FIG. 5 is a block diagram illustrating a concrete configuration of a signal processing portion in the bending instruction portion in FIG. 4.
Figure 6:
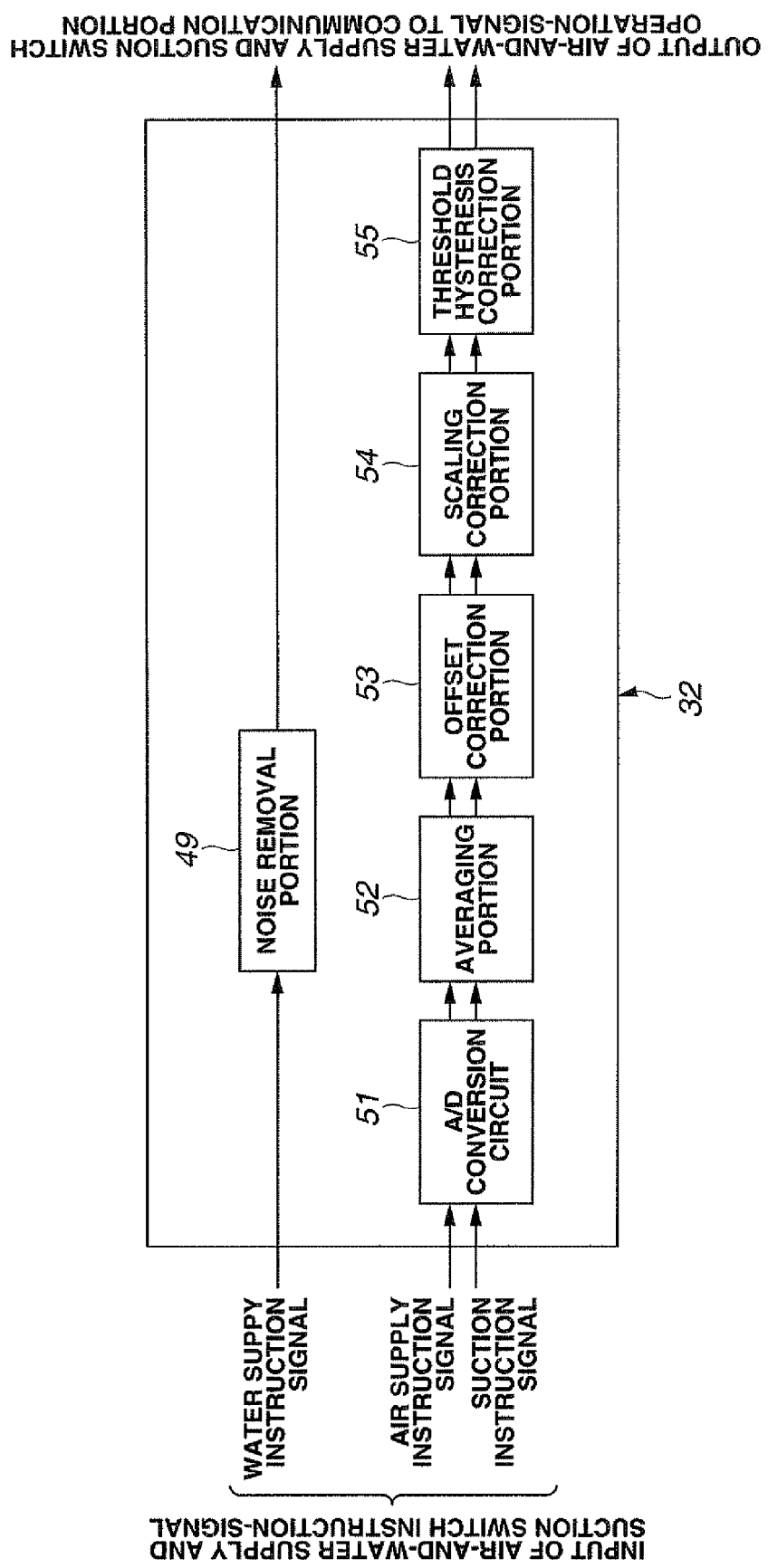
FIG. 6 is a block diagram illustrating a concrete configuration of a signal processing portion in the air-and-water supply and suction switch in FIG. 4.
Figure 7:
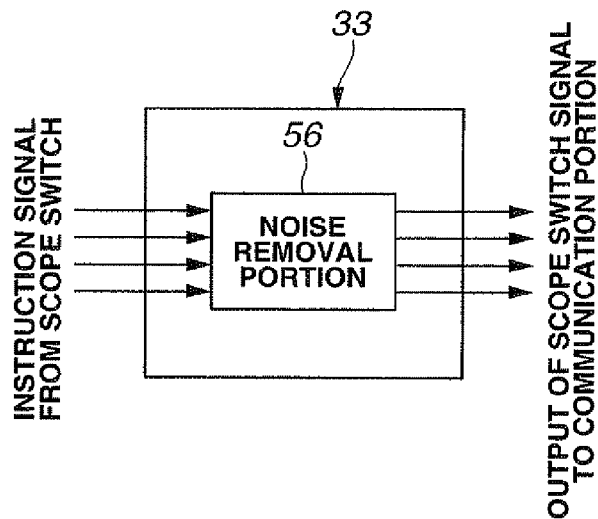
FIG. 7 is a block diagram illustrating a concrete configuration of a signal processing portion in the scope switch in FIG. 4.

The configuration of the operation portion 9 is described below with reference to FIG. 1 and FIGS. 3 to 7. FIG. 3 is a schematic configuration diagram of the operation portion illustrated in FIG. 1. FIG. 4 is a block diagram illustrating the configuration of the control portion in FIG. 3. FIG. 5 is a block diagram illustrating a concrete configuration of the signal processing portion in the bending instruction portion in FIG. 4. FIG. 6 is a block diagram illustrating a concrete configuration of the signal processing portion in the air-and-water supply and suction switch in FIG. 4. FIG. 7 is a block diagram illustrating a concrete configuration of a signal processing portion in the scope switch in FIG. 4.

As illustrated in FIG. 1, the operation portion 9 is provided with a bending instruction portion 9A being bending instruction portion, an air-and-water supply and suction switch 9B and a scope switch 9C.

The bending instruction portion 9A is adapted to be fitted to the operation portion 9 at the time of production. The fitted bending instruction portion 9A outputs, for example, a voltage value as an instruction signal according to the state in which the bending instruction portion 9A instructs. The instruction signal is subjected to a signal processing at the control portion 30 and outputted as a bending instruction portion operation-signal for giving the bending portion 17 instructions about a bending state. As the bending instruction portion 9A, a joystick is used, for example.

Although the present embodiment describes the configuration in which the joystick is used as the bending instruction portion 9A, the present invention is not limited to the embodiment. For example, a track ball may be used to configure the bending instruction portion 9A. In the following description, however, the joystick 9A is used as the bending instruction portion 9A.

The joystick 9A instructs the bending portion 17 to bend in such a manner that a stick portion 9a is tilted to change a tilting direction and a tilting angle. That is to say, the direction in which the joystick 9A is tilted corresponds to the bending directions of the bending portion 17 (or, UP, DOWN, LEFT and RIGHT directions and a combination of those directions) and the angle at which the joystick 9A is tilted corresponds to a bending angle. For example, when the stick portion 9a of the joystick 9A stands upright, the bending portion 17 is in a non-bending state (or, in a straightened state).

The joystick 9A outputs an UP and DOWN direction instruction signal (hereinafter referred to as a "UD direction instruction signal") and a LEFT and RIGHT direction instruction signal (hereinafter referred to as an "RL direction instruction signal") as a signal for instructions to the bending portion 17.

The air-and-water supply and suction switch 9B is the one for giving instructions about supplying air to the air supply pipe 7a, water to the water supply pipe 7b and sucking at the suction pipe 7c of the endoscope 2, generates and outputs an air-and-water supply and suction switch instruction-signal such as an air supply instruction signal, a water supply instruction signal and a suction instruction signal.

The scope switch 9C is the one for performing the control of the image processing device 5 such as freezing the endoscope image displayed on the screen on the monitor 8 and releasing in which a still picture of an endoscope image is recorded in the recording portion (not shown) and is composed of four switches, for example. A user can allocate desired functions to the four switches at discretion.

The scope switch 9C is not limited to the configuration in which the four switches are provided, but may be composed of one or plural switches.

As illustrated in FIG. 3, the joystick 9A, the air-and-water supply and suction switch 9B and the scope switch 9C are electrically connected to the control portion 30 provided in the operation portion 9 respectively.

For this reason, the control portion 30 is supplied with the bending instruction portion instruction-signal from the joystick 9A, the air-and-water supply and suction switch instruction-signal from the air-and-water supply and suction switch 9B and the scope switch instruction-signal from the scope switch 9C.

The control portion 30 outputs an operation signal obtained by subjecting the supplied various instruction signals to signal processing such as correction process to the control device 4 of the control unit 3 by a serial communication, for example.

The configuration of the control portion 30 provided in the operation portion 9 is described below with reference to FIG. 4.

As illustrated in FIG. 4, the control portion 30 includes a bending-instruction portion signal-processing portion 31 to which the bending instruction portion instruction-signal is inputted from the joystick 9A, an air-and-water supply and suction switch signal-processing portion 32 to which the air-and-water supply and suction switch instruction-signal is inputted from the air-and-water supply and suction switch 9B, a scope switch signal-processing portion 33 to which a scope switch instruction-signal is inputted from the scope switch 9C and a communication portion 34 which receives output signals (operation signals) from the three signal processing portions 31 to 33, performs a serial communication with, for example, the control unit 3 and outputs received operation signals to the control unit 3.

The concrete configurations of the bending-instruction portion signal-processing portion 31, the air-and-water supply and suction switch signal-processing portion 32 and the scope switch signal-processing portion 33 are described with reference to FIGS. 5 to 7.

The air-and-water supply and suction switch signal-processing portion 32 is described below. As illustrated in FIG. 6, the air-and-water supply and suction switch signal-processing portion 32 includes a noise removal portion 49, an A/D conversion circuit 51, an averaging portion 52, an offset correction portion 53, a scaling correction portion 54 and a threshold hysteresis correction portion 55.

The water supply instruction signal is inputted to the noise removal portion 49. The water supply instruction signal is an ON/OFF signal, for example. For this reason, the noise removal portion 49 subjects the inputted water supply instruction signal to, for example, a chattering prevention process to prevent turning ON/OFF inadvertently by the influence of, for example, an external noise and a noise contained in the inputted water supply instruction signal.

This enables the noise removal portion 49 to remove the noise and output the air supply operation signal suitable for preventing the occurrence of malfunction.

The air supply instruction signal and the suction instruction signal being analog signals are inputted to the A/D conversion circuit 51. The A/D conversion circuit 51 converts the air-supply instruction signal and the suction instruction signal being the inputted analog signals to digital signals and outputs the digital signals to the averaging portion 52 at the rear stage.

The averaging portion 52 is composed of a moving average filter, for example. Due to this, the averaging portion 52 removes noise components of the inputted digitized air-supply instruction signal and the suction instruction signal through the moving average filter and outputs them to the offset correction portion 53 at the rear stage.

The offset correction portion 53 subjects the input instruction signal to an offset correction process, for example, to cause the center value of the output range of each instruction signal to coincide with a reference value when the air-and-water supply and suction switch 9B is changed over to an air-and-water supply and suction switch which is different in a depression amount from the switch 93 or when the air-and-water supply and suction switch 9B is changed over to another individual which is the same type as the switch 9B.

In this case, if an amount by which the air-and-water supply and suction switch 9B is depressed from a non-contact state is taken as "x," the voltage of the output instruction signal is taken as "y" and the relationship between the depression amount x and the voltage of the output instruction signal y is taken as:

$$y = a \cdot x + b \quad \text{(Equation 1)},$$

(where, "a" and "b" are taken as values inherent in each air-and-water supply and suction switch 9B), the offset correction portion 53 subjects the input instruction signal to a correction process in which the values "b" inherent in each air-and-water supply and suction switch are matched and outputs the result to the scaling correction portion 54 at the rear stage.

The offset correction portion 53 includes a storing portion (not shown) for storing a reference value required for the correction process (offset correction) in which the values "b" inherent in each air-and-water supply and suction switch are matched.

The scaling correction portion 54 subjects the output signal of the offset correction portion 53 to a process in which the values "a" inherent in each air-and-water supply and suction switch 9B in the equation 1 are corrected.

This outputs an instruction signal with the same output range to the threshold hysteresis correction portion 55 at the rear stage when the air-and-water supply and suction switch 9B is changed over to another air-and-water supply and suction switch which is different in a depression amount from the switch 9B or when the air-and-water supply and suction switch 9B is changed over to another individual which is the same type as the switch 9B.

When the amount of air supply, water supply and suction are changed over in a multi-step manner, a signal corresponding to the amount of depression of changeover needs to be set as a signal for changeover timing (threshold).

In order to prevent inadvertent changeovers of the amount of air supply, water supply and suction in the vicinity of the threshold, a hysteresis correction is generally known as means of prevention.

The threshold hysteresis correction portion 55 subjects the output signal from the scaling correction portion 54 to an adjustment process for the threshold of changeover timing and the hysteresis correction process of the output signal.

Specifically, at the adjustment process of the threshold, when the output signal of the scaling correction portion 54 is 0 to 60, for example, 10 and 30 are set as thresholds, for example. When the output signal of the scaling correction portion 54 is 0 to 10, a process is performed to output 0, for example, as the output signal after the adjustment process of the threshold. When the output signal of the scaling correction portion 54 is 10 to 30, a process is performed to output 1, for example, as the output signal after the adjustment process of the threshold. When the output signal of the scaling correction portion 54 is 30 to 60, a process is performed to output 2, for example, as the output signal after the adjustment process of the threshold.

The hysteresis correction process performs such that, when the output signal after the adjustment process of the threshold becomes 0 to 1 in the above example, for example, the changeover timing is taken as 12, for example, and when the output signal after the adjustment process of the threshold becomes 1 to 0 in the above example, for example, the changeover timing is taken as 8, for example.

This enables outputting the same operation signal without causing the deviation of the changeover timing to the control unit 3 through the communication portion 34 even when the air-and-water supply and suction switch 9B is changed over to another air-and-water supply and suction switch which is different in depression amount from the switch 9B or the air-and-water supply and suction switch 913 is changed over to another individual which is the same type as the switch 9B.

In the present embodiment, the noise removal portion 49, the averaging circuit 52, the offset correction portion 53, the scaling correction portion 54 and the threshold hysteresis correction portion 55 in the air-and-water supply and suction switch signal-processing portion 32 may be configured to perform various processes by software in the control portion 30 or configured using a digital process circuit for processing a digital signal.

The scope switch signal-processing portion 33 is described below. As illustrated in FIG. 7, the scope switch signal-processing portion 33 includes a noise removal portion 56.

A first to a fourth scope switch instruction-signals are inputted to the noise removal portion 56 respectively. The first to fourth scope switch instruction-signals are ON/OFF signals, for example. For this reason, as is the case with the noise removal portion 49 of the air-and-water supply and suction switch signal-processing portion 32, the noise removal portion 56 subjects the inputted scope switch instruction-signals to, for example, a chattering prevention process to prevent turning ON/OFF inadvertently by the influence of, for example, an external noise and a noise contained in the inputted scope switch instruction-signal.

This enables the noise removal portion 56 to remove the noise and output the scope switch operation signals suitable for preventing the occurrence of malfunction to the communication portion 34. The scope switch operation signals are outputted to the control unit 3 by the communication portion 34 respectively.

Incidentally, in the air-and-water supply and suction switch signal-processing portion 32, the reference value in the offset correction portion 53, the value "a" inherent in each air-and-water supply and suction switch in the scaling correction portion 54 and the threshold in the threshold hysteresis correction portion 55 may be changed at discretion by input setting operation using the PC 10 capable of capturing data through communication with the control unit 3 by the communication portion 34.

The configuration and the contents of processes of the bending-instruction portion signal-processing portion 31 which are the features of the present embodiment are described below with reference to FIG. 5 and FIGS. 8 to 22.

The concrete configuration of the bending-instruction portion signal-processing portion 31 illustrated in FIG. 4 is illustrated in FIG. 5.

As illustrated in FIG. 5, the bending-instruction portion signal-processing portion 31 includes a correction algorithm calculating portion 40 being correction algorithm portion in which the output range of instruction signals inherent in each joystick 9A is converted to coincide with the predetermined output range of the bending instruction portion operation-signal being the operation signal outputted by the operation portion 9 to generate the bending instruction portion operation-signal, for example, for a joystick being the bending instruction portion 9A attached to the operation portion 9.

The bending-instruction portion signal-processing portion 31 also includes an A/D conversion circuit 41. An analog bending instruction portion instruction-signal is inputted to the A/D conversion circuit 41.

The A/D conversion circuit 41 converts the inputted analog instruction signal (or, the bending instruction portion instruction-signal) to a digital signal and outputs the digital signal to the correction algorithm calculating portion 40 at the rear stage.

As illustrated in FIG. 5, the correction algorithm calculating portion 40 includes an averaging portion 42, an offset correction portion 43, a static noise removal portion 44, a reference axis correction portion 45, a twist correction portion 46 and a scaling correction portion 47. The calculating portions generate the bending instruction portion operation-signal respectively.

Incidentally, in the present embodiment, although the averaging portion 42, the offset correction portion 43, the static noise removal portion 44, the reference axis correction portion 45, the twist correction portion 46 and the scaling correction portion 47 in the correction algorithm calculating portion 40 are configured to perform various correction processes by software in the control portion 30, the various correction processes may be configured using a digital process circuit for processing a digital signal, for example.

The output signal of the A/D conversion circuit 41 is inputted to the averaging portion 42. The averaging portion 42 performs an averaging process such that, for example, n pieces out of the inputted output signal of the A/D conversion circuit 41 are sampled for each predetermined time "t" and the obtained sum of n pieces is divided by "n" to determine an average value.

In other words, the output signal of the A/D conversion circuit 41 may include noise components, however, the averaging process of the averaging portion 42 provides the bending instruction portion instruction-signal with a relatively small number of noise components.

The averaging portion 42 outputs the averaged bending instruction portion instruction-signal to the offset correction portion 43 at the rear stage.

The offset correction portion 43 and the succeeding correction portions are described with reference to FIGS. 8 to 22.

In the following description of the present embodiment, a correction process is regarded to be performed in advance according to the joystick 9A attached to the operation portion 9 at a production process in the manufacturing factory before the electric bending endoscope device 1 is shipped from the manufacturing factory. To simplify description, the case is described with reference to the drawings where, for example, the joystick 9A having a reference instruction range in advance is changed over to a joystick having an instruction range larger than the reference instruction range.

Figure 8:
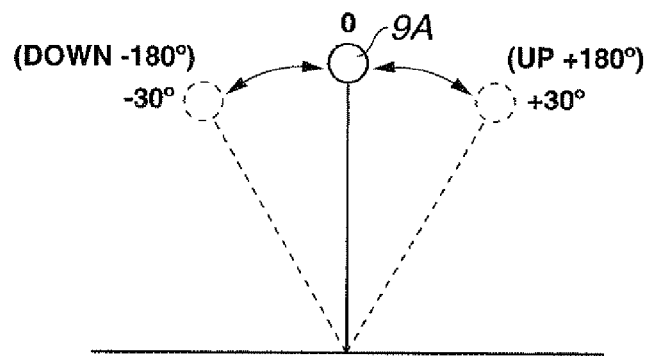
FIG. 8 is a diagram illustrating a reference joystick whose instruction range is ±30 degrees with respect to a neutral position.
Figure 9:
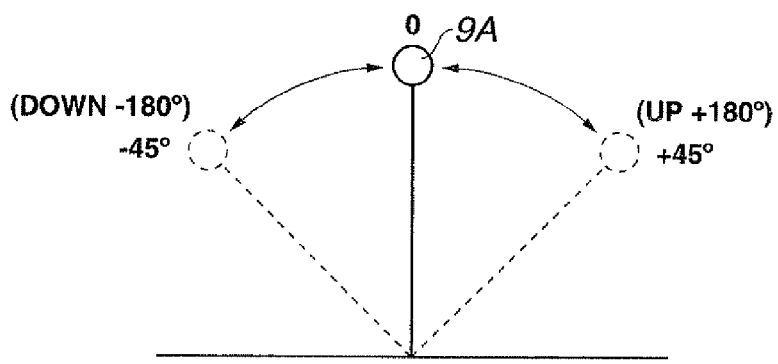
FIG. 9 is a diagram illustrating a reference joystick whose instruction range is ±45 degrees with respect to a neutral position.

FIG. 8 is a diagram illustrating a reference joystick whose instruction range is ±30 degrees with respect to a neutral position. FIG. 9 is a diagram illustrating a joystick whose instruction range is ±45 degrees with respect to a neutral position.

Figure 10:
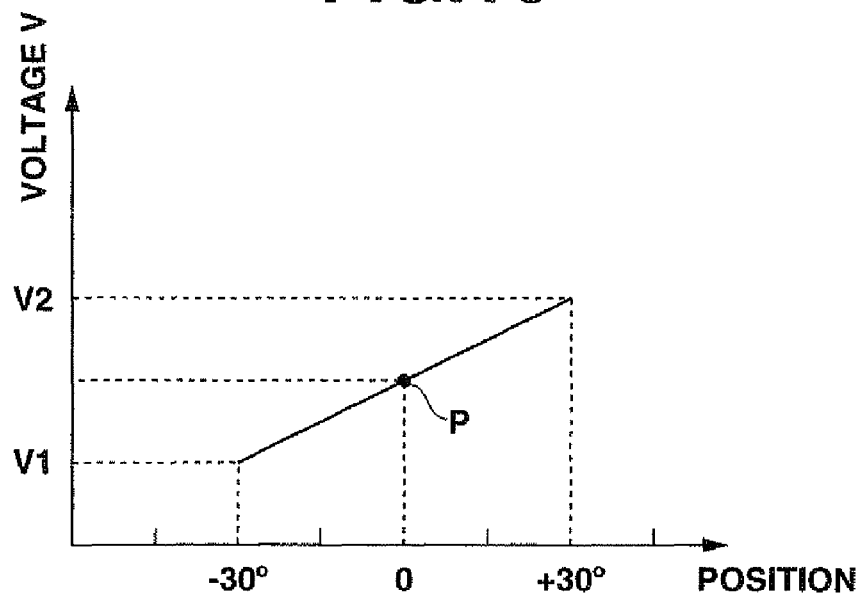
FIG. 10 is a graph illustrating a relationship between the position of instruction range of the joystick in FIG. 8 and the output voltage of the bending instruction portion instruction-signal.
Figure 11:
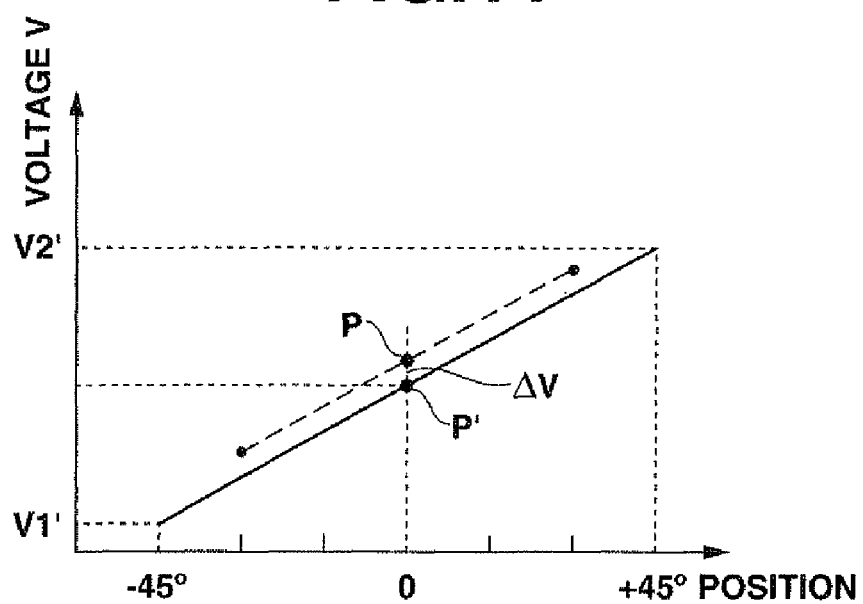
FIG. 11 is a graph illustrating a relationship between the position of instruction range of the joystick in FIG. 9 and the output voltage of the bending instruction portion instruction-signal.

FIG. 10 is a graph illustrating a relationship between the position of instruction range of the joystick in FIG. 8 and the output voltage of the bending instruction portion instruction-signal. FIG. 11 is a graph illustrating a relationship between the position of instruction range of the joystick in FIG. 9 and the output voltage of the bending instruction portion instruction-signal.

Incidentally, FIGS. 8 and 9 illustrate the endoscope 2 with the bending portion 17 whose bendable angle is, for example, ±180 degrees in the UP and the DOWN direction respectively. The bendable angle of the bending portion 17 is ±160 degrees in the LEFT and the RIGHT direction respectively, but an illustration is omitted to simplify the description thereof.

When the joystick 9A is changed over to a joystick which is different from the joystick 9A in the instruction range where instructions for the bending operation are inputted, the offset correction portion 43 in FIG. 5 subjects the inputted bending instruction portion instruction-signal to an offset correction process so that the center points of voltage value of the bending instruction portion operation-signals are caused to coincide with each other, for example.

That is to say, the offset correction portion 43 performs the offset correction process to correct the difference between the output voltages of the bending instruction portion instruction-signals caused by the difference in types of and the individual difference of the joystick 9A being the bending instruction portion.

For example, in the reference joystick 9A illustrated in FIG. 8, if the output voltage of the bending instruction portion instruction-signal at a tilting angle (a tilting position) of the stick portion 9a of −30 degrees is taken as V1 and the output voltage of the bending instruction portion instruction-signal at a tilting angle of the stick portion 9a of +30 degrees is taken as V2, the output voltages V1 and V2 of the bending instruction portion instruction-signal have such a characteristic as to be illustrated in the graph in FIG. 10 with respect to the tilting angle of the stick portion 9a.

The center point P between the output voltages of the bending instruction portion instruction-signal having such a characteristic corresponds to a neutral position of 0 degrees of the stick portion 9a.

In the case where a joystick to be changed over is the joystick 9A illustrated in FIG. 9, if the output voltage of the bending instruction portion instruction-signal at a tilting angle (a tilting position) of the stick portion 9a of −45 degrees is taken as V1' and the output voltage of the bending instruction portion instruction-signal at a tilting angle of the stick portion 9a of +45 degrees is taken as V2', the output voltages V1' and V2' of the bending instruction portion instruction-signal have such a characteristic as to be illustrated in the graph in FIG. 11 with respect to the tilting angle of the stick portion 9a.

The center point P' between the output voltages of the bending instruction portion instruction-signal having such a characteristic corresponds to a neutral position of 0 degrees of the stick portion 9a, however, the center point P' deviates from the center point P between the output voltages of the reference joystick 9A in FIG. 8 by ΔV (refer to FIG. 11).

Then, the offset correction portion 43 offsets the center point P' between the output voltages of the bending instruction portion instruction-signal of the joystick 9A by ΔV when a joystick is changed over to the joystick 9A in FIG. 9 to cause the center point P' to coincide with the center point P between the output voltages of the reference joystick 9A.

This allows correcting a difference between offset voltages of the output voltages of the bending instruction portion instruction-signal caused by the difference in types of and the individual difference of the joystick 9A.

The offset correction portion 43 outputs a signal subjected to the offset correction process to the static noise removal portion 44.

Figure 12:
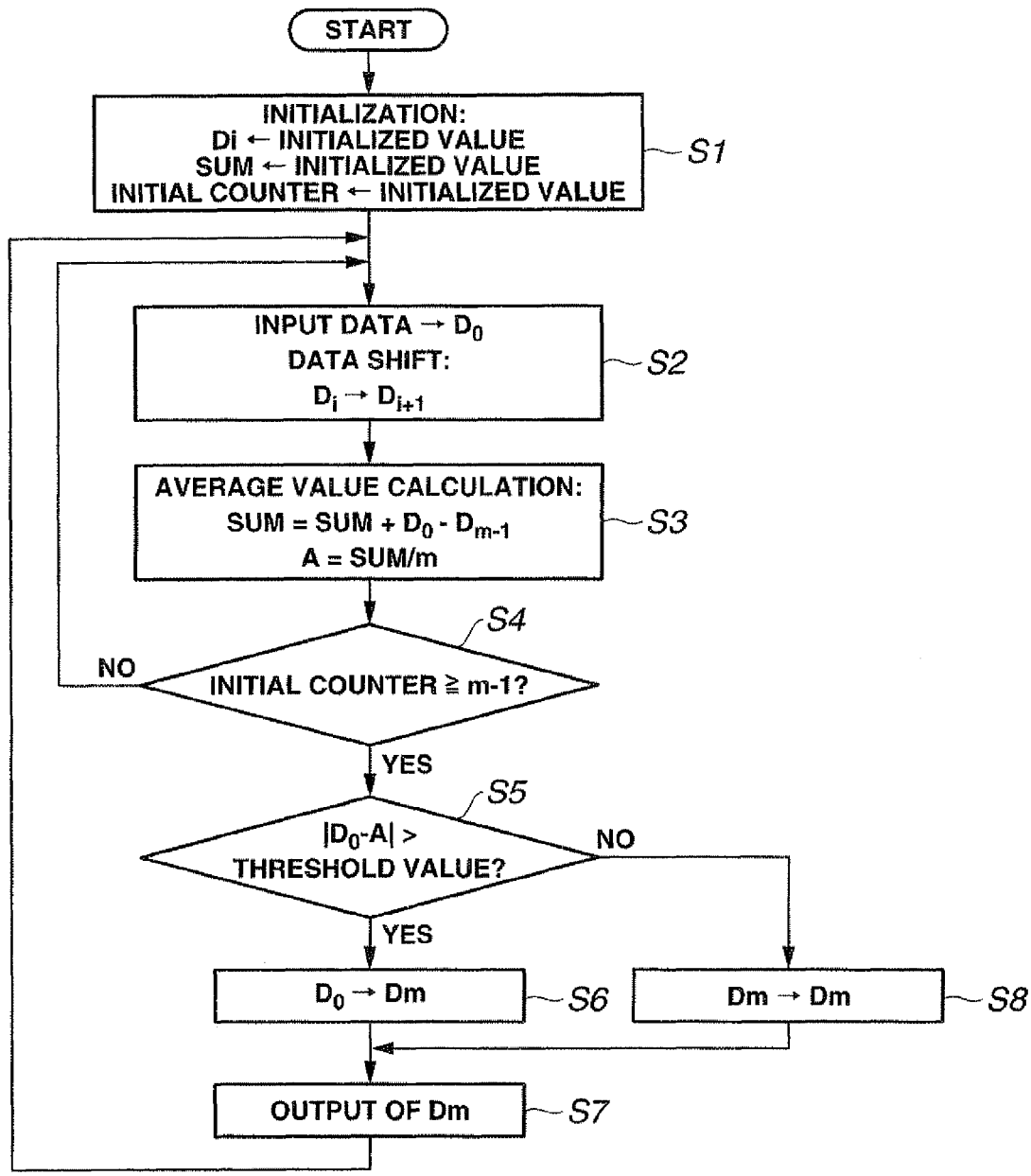
FIG. 12 is a flow chart illustrating a program of one example of noise removing process executed by a static noise removing portion.

FIG. 12 is a flow chart illustrating a program of one example of noise removing process executed by a static noise removing portion.

The static noise removal portion 44 performs a process for removing noise components included in the inputted signal after the offset correction process.

In the relationship between the output voltage V of the signal after the offset correction process and the elapsed time "t", of which illustration is omitted though, the output voltage varies during a predetermined period for which a bending instruction is changed (or, the joystick is being moved), but, the output voltage is substantially constant during the period except the above (or, during the period for which a bending instruction is fixed). The noise components are relatively increased particularly in the instruction signal during the predetermined period (or, the period for which the bending instruction is fixed) for which the output voltage is substantially constant, so that the noise components need to be removed.

For this reason, the static noise removal portion 44 uses, for example, the moving average filter and the hysteresis process to remove noise components included in the signal after the offset correction process.

As one example of a noise removing process method using the moving average filter and the hysteresis process, there is a program illustrated in FIG. 12.

The process steps are described with reference to FIG. 12. As illustrated in FIG. 12, at step S1, the static noise removal portion 44 initializes the voltage value Di of the signal from the offset correction process, the total voltage value SUM and the initial counter.

At step S2, the inputted voltage value of the signal after the offset correction process is received as D0. The voltage value Di of the input signal after the elapse of a predetermined time is data-shifted and received as D(i+1).

At step S3, the voltage value of the signal after the offset correction process within the predetermined time is averaged. That is to say, the total voltage value SUM is determined such that the voltage value D0 being the renewed input data is added to the total voltage value SUM within the previous predetermined time, from which the voltage value D(m−1) (where, "m" is the number of taps in the case where a so-called FIR filter is used and is 64, for example) being the earliest data is subtracted.

Dividing the obtained total voltage value SUM by the number of taps "m" provides an averaged output voltage value A.

At a determination process of step 4, a determination is made as to whether the counter value of the initial counter exceeds the number of taps of m−1. If the counter value exceeds the number of taps of m−1, the process proceeds to step 5. If not, the process returns to step 2 to repeat the process. That is to say, a method of averaging time series data is used herein.

At a determination process of the step 5, a determination is made as to whether the voltage value in which the average voltage value A is subtracted from the voltage value D0 of the latest input signal is greater than a predetermined threshold.

If the voltage value is determined to be greater than the predetermined threshold, at step S6, the voltage value D0 of the latest input signal is held in an output buffer (not shown) as a buffer output data Dm and the process proceeds to step S7.

On the other hand, if the voltage value is determined to be smaller than the predetermined threshold at a determination process of the step 5, the buffer output data Dm being the voltage value held in the output buffer (not shown) is held again as a buffer output data Dm at step S8, and the process proceeds to step S7.

At step S7, the static noise removal portion 44 is controlled to output the output buffer data Dm held in the output buffer (not shown), the process returns to the step S2 and subsequent processes are repetitively executed in the similar manner.

The execution of the calculation process based on such a program allows the bending instruction portion instruction-signal to be outputted as it is to the reference axis correction portion 45 at the rear stage during the predetermined period for which the bending instruction is being changed. Furthermore, the bending instruction portion instruction-signal whose noise components are removed can be outputted to the reference axis correction portion 45 at the rear stage during the predetermined period for which the bending instruction is being fixed.

The configuration and the contents of processes of the reference axis correction portion 45 are described below with reference to FIGS. 13 to 15.

Figure 13:
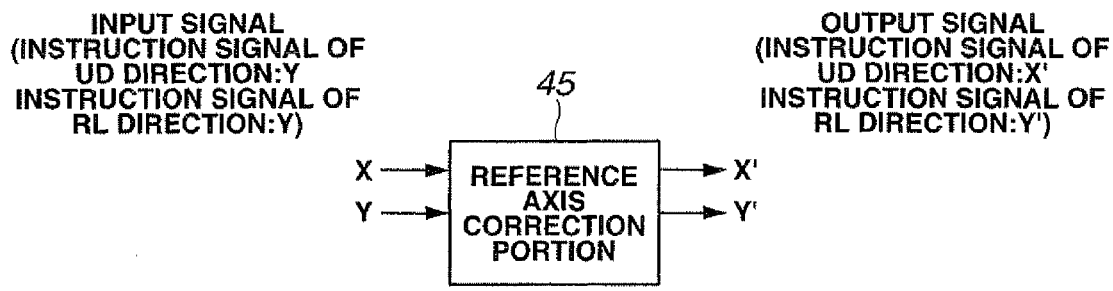
FIG. 13 is a schematic diagram illustrating the configuration of a reference axis correction portion.

FIG. 13 is a schematic diagram illustrating the configuration of the reference axis correction portion. FIG. 14 is an electric signal coordinate diagram of the bending instruction portion instruction-signal according to the bending direction of the bending portion before a reference axis correction process. FIG. 15 is an electric signal coordinate diagram of the bending instruction portion instruction-signal according to the bending direction of the bending portion after the reference axis correction process. Reference numeral 50 indicated by a broken line in FIGS. 14 and 15 denotes the output range of the bending instruction portion instruction-signal of the joystick.

Depending on an operator using the operation portion 9, the direction in which the operator wants to actually bend the bending portion 17 may sensuously deviate from the direction in which the operator tilts the stick portion 9a of the joystick 9A.

Then, in the present embodiment, the reference axis correction portion 45 corrects an angle deviated from a predetermined reference axis with respect to the inputted bending instruction portion instruction-signal to remove the deviation.

Specifically, as illustrated in FIG. 13, the reference axis correction portion 45 performs the reference axis correction process such that, if the input signal in the UD direction being the inputted bending instruction portion instruction-signal is taken as X and the input signal in the RL direction is taken as Y, the output signal X' in the UD direction and the output signal Y' in the RL direction being output signals of which angles deviated from the predetermined reference axis are corrected are provided.

The correction process in the reference axis correction portion 45 is performed by the calculation process based on the following equations 2 and 3. An angle deviated from the reference axis is taken as θ.

[Equation 2]

$$X' = X \cos\theta - Y \sin\theta \qquad \text{(Equation 2)}$$

[Equation 3]

$$Y' = X \sin\theta + Y \cos\theta \qquad \text{(Equation 3)}$$

Figure 14:
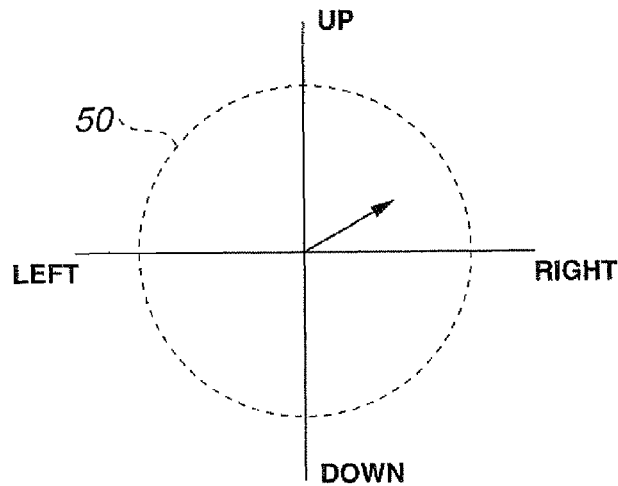
FIG. 14 is an electric signal coordinate diagram of the bending instruction portion instruction-signal according to the bending direction of the bending portion before the reference axis correction process.
Figure 15:
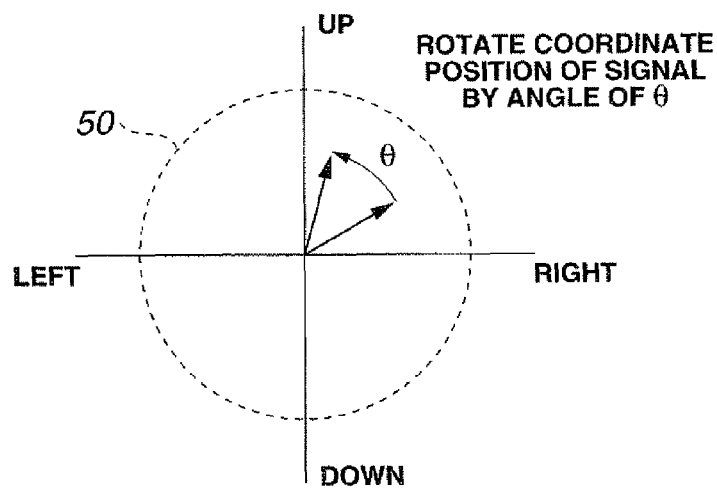
FIG. 15 is an electric signal coordinate diagram of the bending instruction portion instruction-signal according to the bending direction of the bending portion after the reference axis correction process.

The above equations 2 and 3 enable providing the output signal X' in the UD direction and the output signal Y' in the RL direction which are adjusted to the angle θ deviated from the predetermined reference axis as illustrated in FIGS. 14 and 15, for example.

This provides the bending instruction portion instruction-signal capable of causing the direction in which the operator wants to actually bend the bending portion 17 to coincide with the direction in which the operator tilts the stick portion 9a of the joystick 9A and outputs the bending instruction portion instruction-signal to a twist correction portion 46 at the rear stage.

Although the case where the angle θ is predetermined in the reference axis correction portion 45 is described above, the present invention is not limited to the above. For example, a storing portion for storing a plurality of angle data may be provided and any angle data may be selected from among the plurality of angle data stored in the storing portion to set the angle θ. Angle data which the communication portion 34 of the operation portion 9 inputs through the PC 10 is obtained and the angle based on the angle data may be set as the angle θ.

The contents of processes of the twist correction portion 46 are described below with reference to FIGS. 16 to 19.

Figure 16:
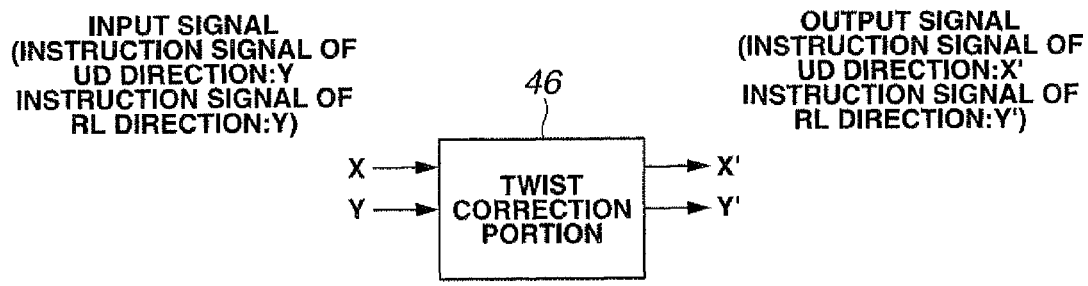
FIG. 16 is a schematic diagram illustrating a twist correction portion.
Figure 17:
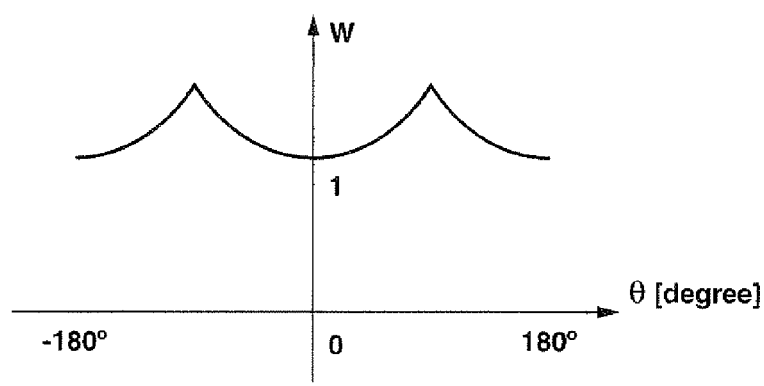
FIG. 17 is a graph illustrating the characteristics of correction values used for correction process in the twist correction portion and the bending direction.
Figure 18:
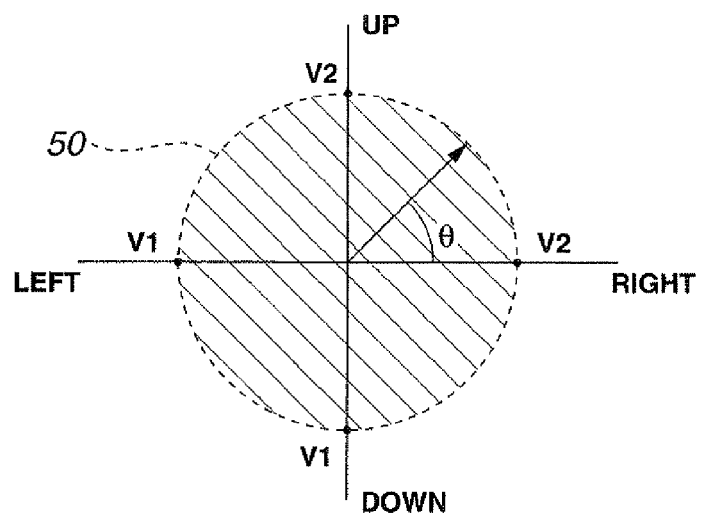
FIG. 18 is an electric signal coordinate diagram of the bending instruction portion instruction-signal according to the bending direction of the bending portion before the twist correction process.
Figure 19:
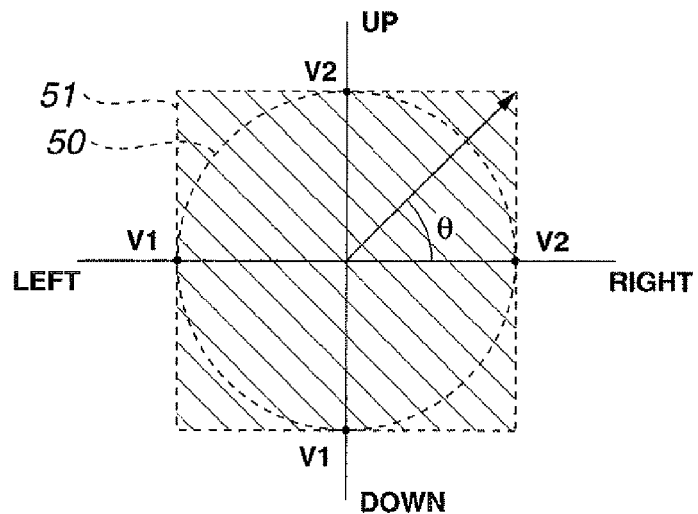
FIG. 19 is an electric signal coordinate diagram of the bending instruction portion instruction-signal according to the bending direction of the bending portion after the twist correction process.

FIG. 16 is a schematic diagram illustrating the configuration of a twist correction portion. FIG. 17 is a graph illustrating the characteristics of correction values used for correction process in the twist correction portion and the bending direction. FIG. 18 is an electric signal coordinate diagram of the bending instruction portion instruction-signal according to the bending direction of the bending portion before the twist correction process. FIG. 19 is an electric signal coordinate diagram of the bending instruction portion instruction-signal according to the bending direction of the bending portion after the twist correction process. Reference numeral 50 indicated by a broken line in FIGS. 18 and 19 denotes the output range of the bending instruction portion instruction-signal of the joystick.

When the endoscope 2 includes the bending portion 17 whose bendable angles in the UP and the DOWN direction are, for example, ±180 degrees respectively and whose bendable angles in the LEFT and the RIGHT direction are, for example, ±160 degrees respectively, the endoscope 2 is required to control the bending portion 17 so as to bend the bending portion 17 to the respective bendable angles (for example, +180 degrees in the UP direction and +160 degrees in the RL direction).

Then, in the present embodiment, the twist correction portion 46 performs a twist correction so that the shape of output range of the inputted bending instruction portion instruction-signal is made similar to the shape of the predetermined bending range in the bending portion 17.

Specifically, as illustrated in FIG. 16, the twist correction portion 46 performs the twist correction process such that, if the input signal in the UD direction being the inputted bending instruction portion instruction-signal is taken as X, and the input signal in the RL direction is taken as Y, the output signal X' in the UD direction and the output signal Y' in the RL direction which are corrected so as to output the shape of the predetermined bending range can be obtained.

The correction process in the twist correction portion 46 is performed by the calculation process based on the following equations 4 to 6. The following correction value is taken as W.

[Equation 4]

$$X' = W \cdot X \quad \text{(Equation 4)}$$

[Equation 5]

$$Y' = W \cdot Y \quad \text{(Equation 5)}$$

In this case, the correction value W is derived from the following equation 6.

[Equation 6]

$$\text{The correction value } W = 1/\max(|\cos \theta|, |\sin \theta|) \quad \text{(Equation 6)}$$

The characteristic of the correction value W according to the bending angle θ is shown in the graph in FIG. 17.

As illustrated in FIGS. 18 and 19, for example, the above equations 4 to 6 enable providing the output signal X' in the UD direction and the output signal Y' in the RL direction which are the bending instruction portion instruction-signals corrected to output the shape of the predetermined bending range.

In other words, the output range 50 of the bending instruction portion instruction-signal of the reference joystick 9A is a circular arc on the electric signal coordinate diagram in FIG. 18.

However, the output range 51 of the bending instruction portion instruction-signal after the twist correction process is converted to a substantial square output range 51 on the electric signal coordinate diagram in FIG. 19 including the output range 50.

That is to say, the difference between the output range 51 and the output range 50 enables the bending portion 17 to be bent in the entire predetermined bending range.

This provides the bending instruction portion instruction-signal subjected to the twist correction so that the bending portion 17 can be bent in the entire bendable range as illustrated in the output range 51, for example, in FIG. 19. Thereafter, the bending instruction portion instruction-signal is outputted to the scaling correction portion 47 at the rear stage.

The contents of processes of the scaling correction portion 47 are described below with reference to FIGS. 20 to 22.

Figure 20:
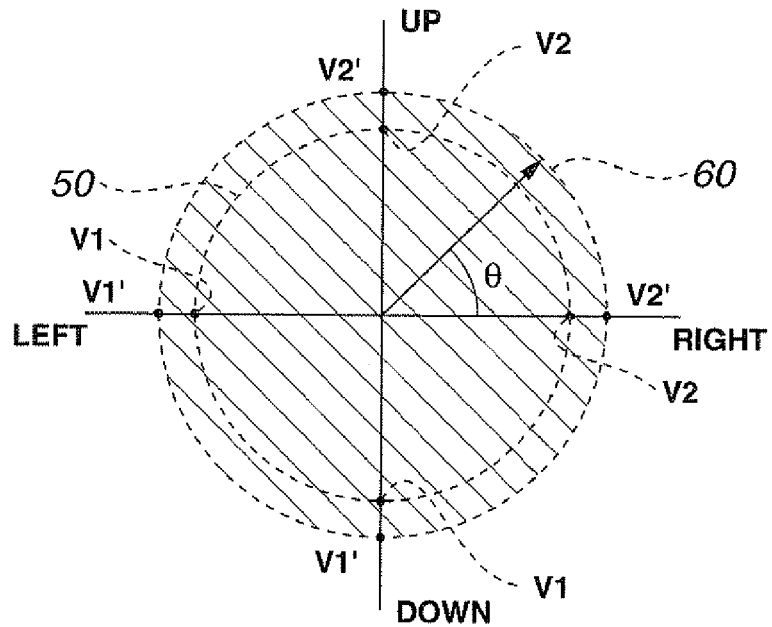
FIG. 20 is an electric signal coordinate diagram of the respective bending instruction portion instruction-signals before the twist correction process in the reference joystick in FIG. 8 and the joystick in FIG. 9.
Figure 21:
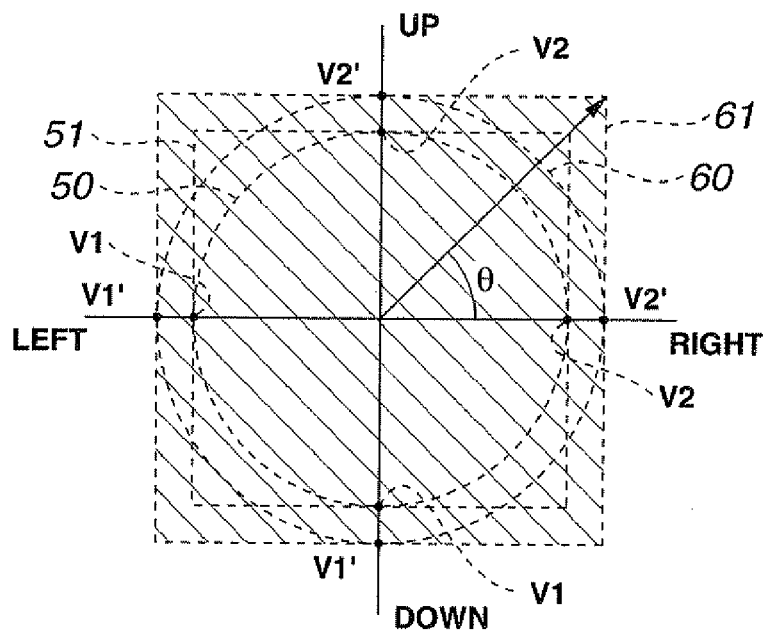
FIG. 21 is an electric signal coordinate diagram of the respective bending instruction portion instruction-signals after the twist correction process corresponding to FIG. 20.
Figure 22:
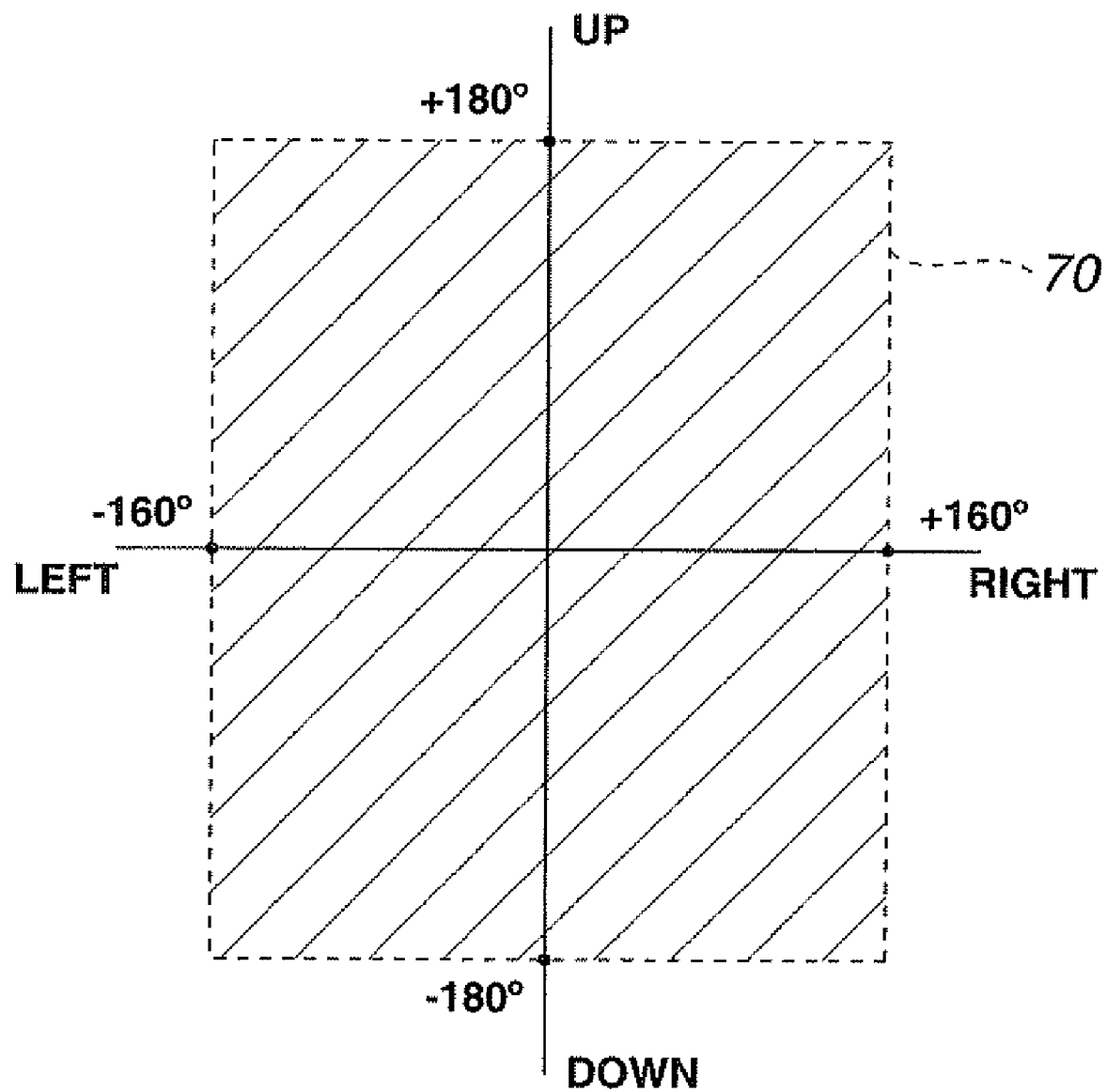
FIG. 22 is an electric signal coordinate diagram after the scaling correction process in which the respective bending instruction portion instruction-signals of the joysticks in FIG. 8 and the joystick in FIG. 9 are converted to the maximum movable range of the same bending portion by the scaling correction portion.

FIGS. 20 to 22 describe the contents of processes of the scaling correction portion 47. FIG. 20 is an electric signal coordinate diagram of the respective bending instruction portion instruction-signals before the twist correction process in the reference joystick in FIG. 8 and the joystick in FIG. 9. FIG. 21 is an electric signal coordinate diagram of the respective bending instruction portion instruction-signals after the twist correction process corresponding to FIG. 20. FIG. 22 is an electric signal coordinate diagram after the scaling correction process in which the output ranges of the bending instruction portion instruction-signals of the reference joystick in FIG. 8 and the joystick in FIG. 9 are converted to the maximum movable range of the same bending portion by the scaling correction portion 47.

FIG. 22 shows the maximum bendable range of the bending portion 17 where the bendable angles in the UP and the DON direction are ±180 degrees respectively and the bendable angles in the LEFT and the RIGHT direction are ±160 degrees respectively, for example.

The bending instruction portion instruction-signal (for example, the bending instruction portion instruction-signal according to the output range 50 in FIG. 19) which the twist correction portion 46 corrected so that the bending portion 17 can be bent in the entire bendable range is inputted to the scaling correction portion 47.

The scaling correction portion 47 performs the scaling correction such that the inputted bending instruction portion instruction-signal is multiplied by a correction multiplying value Z stored in a storing portion (not shown) so that the output range (or, the output range 51 or the output range 61 in FIG. 21) of the bending instruction portion instruction-signal is caused to coincide with the maximum movable range (or, the maximum movable range 70 in FIG. 22) of the bending portion 17.

The correction multiplying value Z may be inputted by the communication portion 34 of the operation portion 9 through the PC 10 at the manufacturing process of the operation portion 9, or a plurality of the correction multiplying values Z provided for each maximum movable range of the bending portion 17 may be stored in advance in a storing portion (not shown) to read a desired correction multiplying value Z if needed to perform the scaling correction process.

An actual scaling correction is described to which the bending instruction portion instruction-signals are subjected which correspond to each of two joysticks: the reference joystick illustrated in FIG. 8; and the joystick illustrated in FIG. 9 which is changed over from the reference joystick.

As described above, if the joystick attached to the operation portion 9 is the reference joystick 9A illustrated in FIG. 8, the output range 50 of the bending instruction portion instruction-signal before the twist correction process is a circular arc on the electric signal coordinate diagram in FIG. 20.

The output range 50 is converted to a substantial square output range 51 on the electric signal coordinate diagram in FIG. 21 including the output range 50 after the twist correction process. Incidentally, the output range 51 corresponds to the voltages V1 and V2 of the bending instruction portion instruction-signal.

In contrast to the above joystick 9A, if a joystick to be changed over is the joystick 9A illustrated in FIG. 9, the output range 60 of the bending instruction portion instruction-signal before the twist correction process is a circular arc on the electric signal coordinate diagram FIG. 20. Incidentally, as an example of individual difference of the joystick illustrated in FIG. 8, the output range 60 may be assumed.

The output range 60 is converted to a substantial square output range 61 on the electric signal coordinate diagram in FIG. 21 including the output range 60 after the twist correction process.

The output range 61 corresponds to the voltages V1' and V2' of the bending instruction portion instruction-signal.

Since the present embodiment has a relationship of the voltage V1'> the voltage V1 and the voltage V2'> the voltage V2, the output range 61 is greater than the output range 51 as illustrated in FIG. 21.

The scaling correction portion 47 subjects the bending instruction portion instruction-signal in the output ranges 51 or 61 to the scaling process.

In this case, if a joystick is the reference joystick illustrated in FIG. 8, the bending instruction portion instruction-signal of the output range 51 is multiplied by the correction multiplying value Z in which the voltage V2 in the UP direction corresponds to 180 degrees, the voltage V1 in the DOWN direction corresponds to −180 degrees, the voltage V2 in the RIGHT direction corresponds to 160 degrees and the voltage V1 in the LEFT direction corresponds to −160 degrees in the output range 51 of the bending instruction portion instruction-signal.

In other words, the correction multiplying value Z at this point is equal to V2·(180/V2), for example, in the UD direction and to V2·(160/V2), for example, in the RL direction.

Therefore, such a scaling correction process causes the output range 51 of the bending instruction portion instruction-signal in the joystick 9A in FIG. 8 to coincide with the maximum movable range 70 of the bending portion 17 in FIG. 22.

On the other hand, if a joystick is the one illustrated in FIG. 9, the bending instruction portion instruction-signal of the output range 51 is multiplied by the correction multiplying value Z1 in which the voltage V2' in the UP direction corresponds to 180 degrees, the voltage V1' in the DOW direction corresponds to −180 degrees, the voltage V2' in the RIGHT direction corresponds to 160 degrees and the voltage V1' in the LEFT direction corresponds to −160 degrees in the output range 61 of the bending instruction portion instruction-signal.

In other words, the correction multiplying value Z1 at this point is equal to, for example, V2'·(180/V2') in the UD direction and to, for example, V2'·(160/V2') in the RL direction.

Therefore, such a scaling correction process causes the output range 61 of the bending instruction portion instruction-signal in the joystick 9A in FIG. 9 to coincide with the maximum movable range 70 of the bending portion 17 in FIG. 22, as is the case with the reference joystick 9A illustrated in FIG. 8.

In the present embodiment, although the maximum movable range 70 of the bending portion 17 is described where the maximum movable angles in the UP and the DOWN direction are, for example, ±180 respectively and the maximum movable angles in the LEFT and the RIGHT direction are, for example, ±160 respectively, the angles may be changed over and set at discretion if required.

As described above, in the present embodiment, providing the correction algorithm calculating portion 40 performing above described correction process in the bending-instruction portion signal-processing portion 31 in operation portion 9 allows the operation portion 9 to output the bending instruction portion operation-signal always with the same output range irrespective of types of the joystick 9A even if, for example, the joystick 9A being the bending instruction portion different in instruction range is changed at the manufacturing process.

Thereby, merely connecting the operation portion 9 of the present embodiment to the control unit 3 enables the electric bending endoscope device 1 to be used without an operation for setting change such as correction process which has been required hitherto when an operator performs a change to the operation portion 9 with the joystick 9A with the predetermined instruction range according to the operator's technique and taste in the electric bending endoscope device 1.

The operator can cause the bending portion 17 to be bent by a normal bending operation irrespective of the instruction range of the changed joystick 9A when the operator uses the electric bending endoscope device 1. This realizes the electric bending endoscope device in which the change work of the operation portion 9 is simplified and user friendliness is improved.

Second Embodiment

Figure 23:
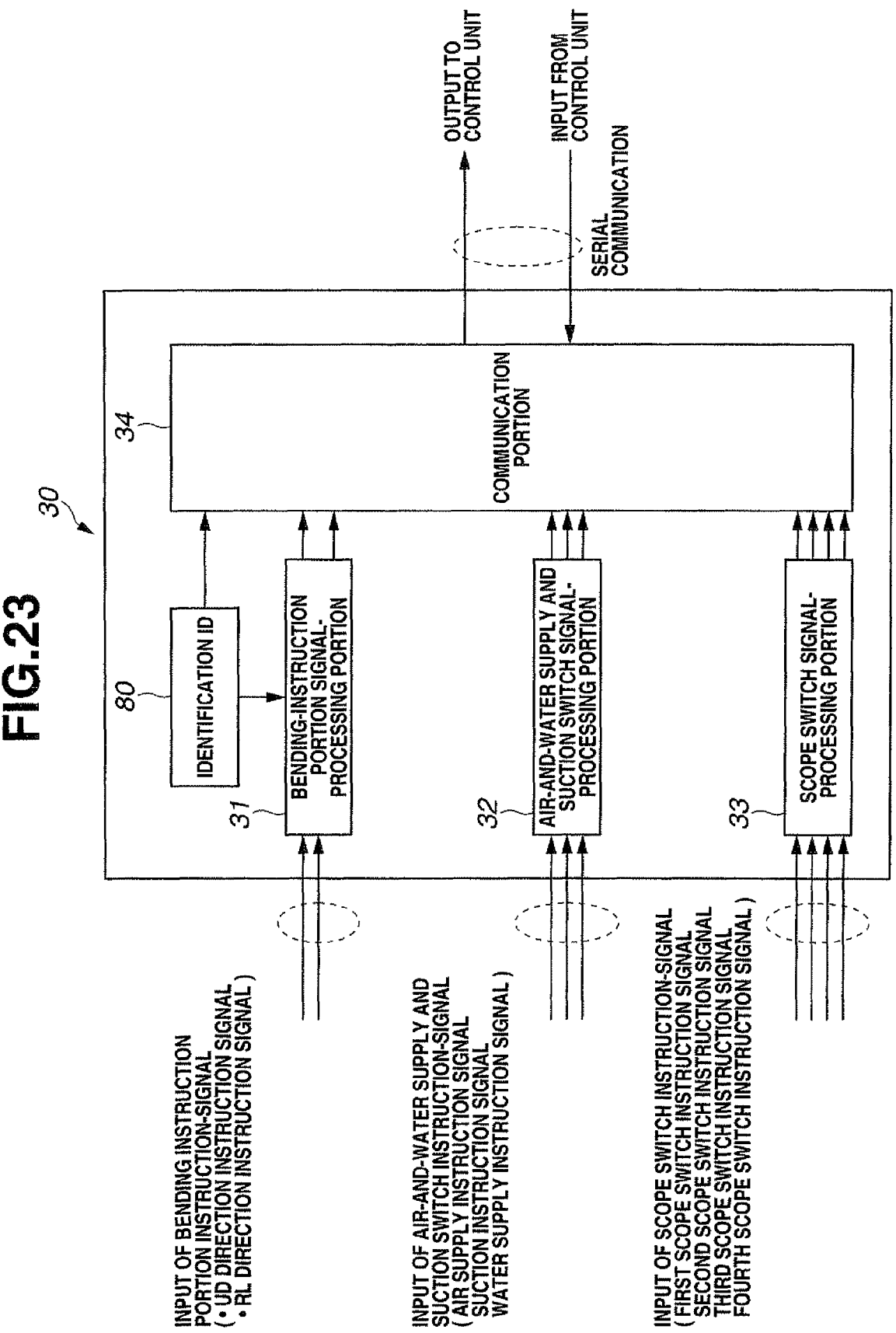
FIG. 23 is a block diagram illustrating the configuration of a control portion provided in the operation portion of the electric bending endoscope device according to a second embodiment of the present invention.
Figure 24:
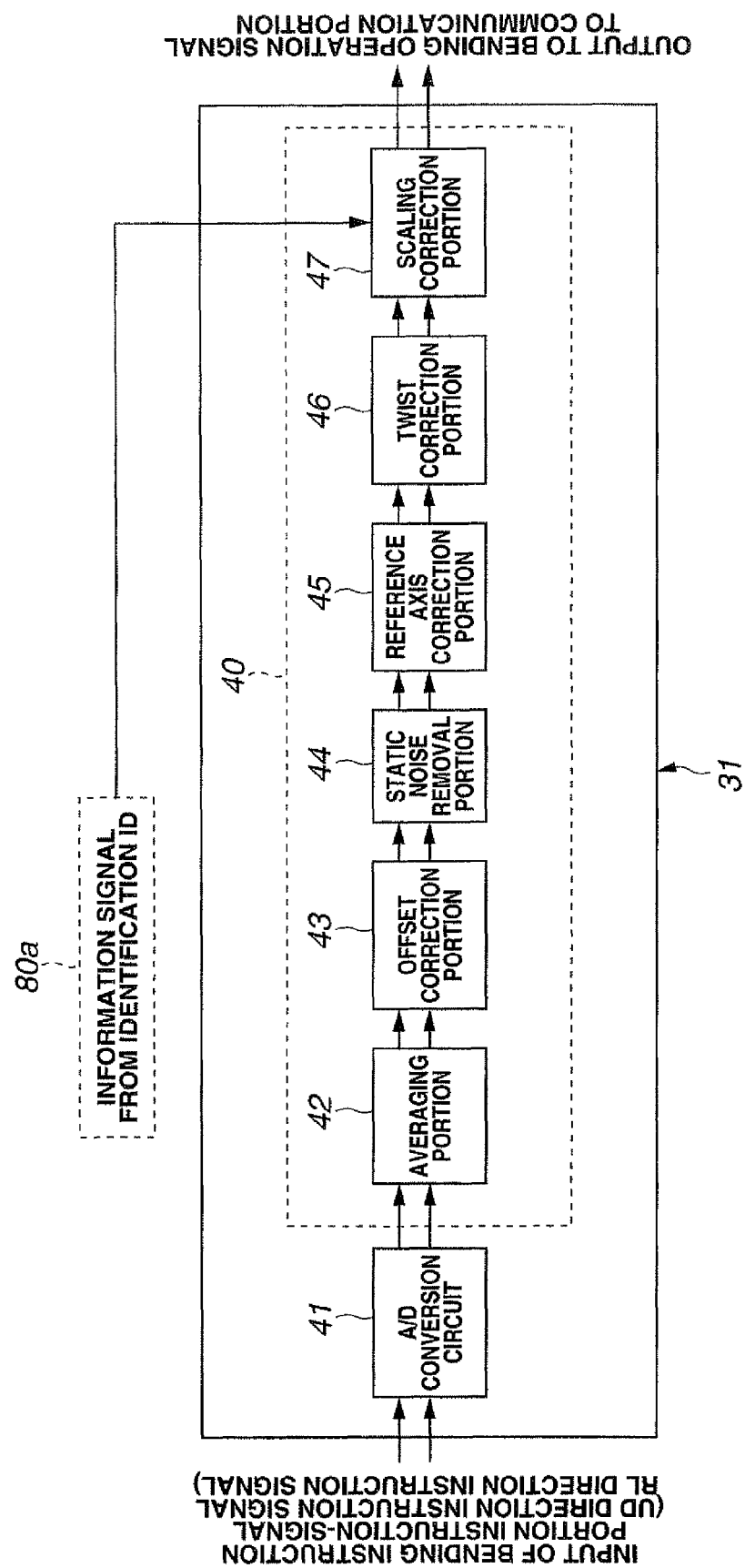
FIG. 24 is a block diagram illustrating a concrete configuration of the signal processing portion in the bending instruction portion in FIG. 23.
Figure 27:
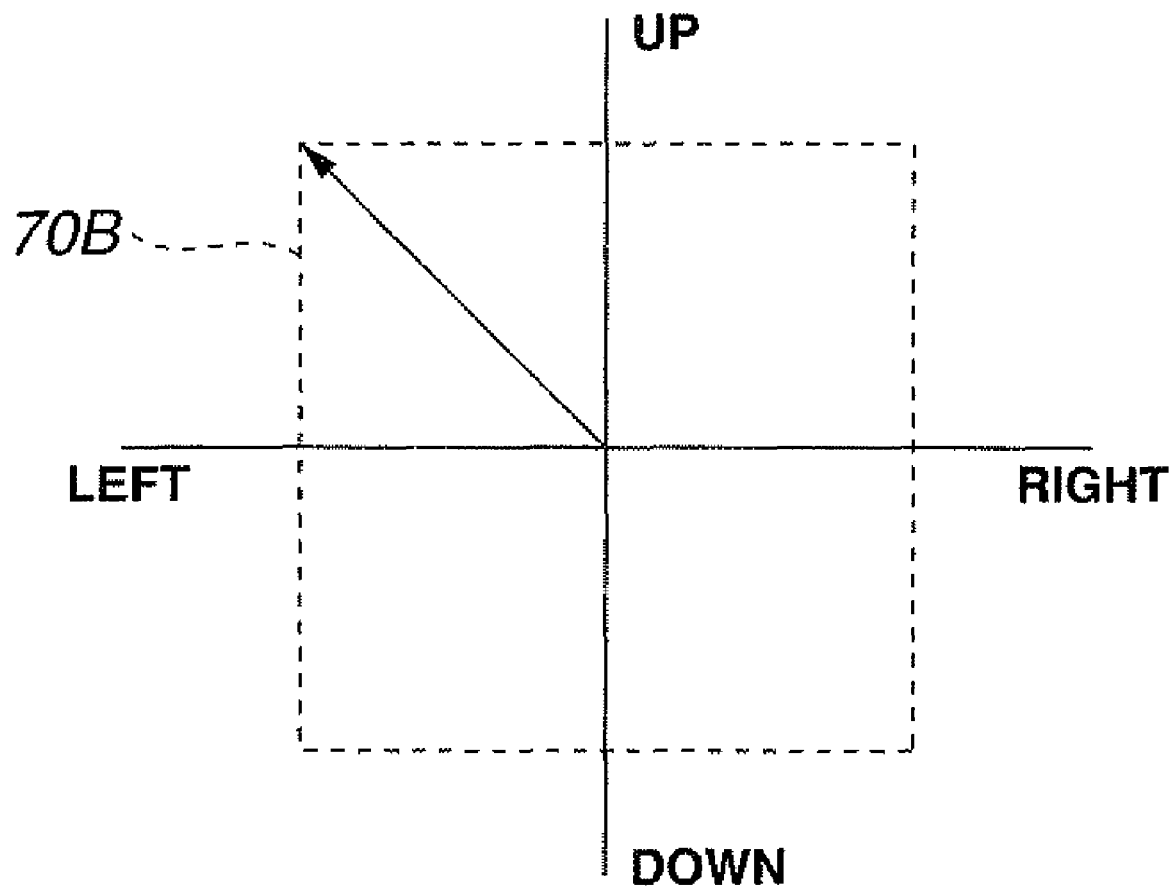
FIG. 27 is an electric signal coordinate diagram of the bending instruction portion instruction-signal after the signal processing in the angle knob mode.

FIGS. 23 to 27 relate to the second embodiment of the electric bending endoscope device of the present invention. FIG. 23 is a block diagram illustrating the configuration of the control portion provided in an operation portion. FIG. 24 is a block diagram illustrating a concrete configuration of the bending instruction portion signal-processing-portion in FIG. 23. FIG. 25 is a diagram for setting the after-mentioned angle mode of the operation portion by a determination process based on information from an identification ID in FIG. 23. FIG. 26 is an electric signal coordinate diagram of the bending instruction portion instruction-signal after signal processing in an after-mentioned game mode. FIG. 27 is an electric signal coordinate diagram of the bending instruction portion instruction-signal after the signal processing in the angle knob mode. In FIGS. 23 and 24, the composing elements, which are the same as those of the first embodiment, are given the same reference numerals and characters to omit the description thereof. Only portions different from those of the first embodiment are described.

In general, the endoscope 2 uses an angle knob mode in which the operator tilts the stick portion 9a of the joystick 9A toward the operator to bend the bending portion 17 to the UP direction and tilts the stick portion 9a toward the other side of the operator to bend the bending portion 17 to the DOWN direction.

Aside from the angle knob mode, as an angle mode, there has been a game mode in which a bending portion is bent in the direction which coincides with the direction in which the bending portion is instructed to bent like a controller for a game machine. That is to say, in the game mode, the operator tilts the stick portion 9a of the joystick 9A toward the operator (toward the lower side) to bend the bending portion 17 to the DOWN direction and tilts the stick portion 9a toward the other side of the operator (toward the upper side) to bend the bending portion 17 to the UP direction.

In consideration of user friendliness of the electric bending endoscope 2, it is desirable to set a mode to the optimum operation mode according to cases and operator's tastes and the like.

In the present embodiment, an identification ID 80 storing various pieces of information such as mode information for setting, for example, the operation mode of the bending instruction portion 9A is provided in the operation portion 9. The operation mode is set such that the sign of the correction multiplying value Z in the UP and the DOWN direction at the time of the scaling correction by the scaling correction portion 47 according to the mode information from the identification ID 80 is changed over to a plus or a minus.

As illustrated in FIG. 23, the identification ID 80 storing various pieces of information such as mode information for setting, for example, the operation mode is provided in the control portion 30 of the operation portion 9.

Incidentally, the identification ID 80 may store not only the mode information, but also control system information such as I/F device information, absolute position control and relative position control based on, for example, the bending instruction portion 9A and information required for air-and-water supply and suction operation.

For example, mode identification information of "0" and "1" is stored in the identification ID 80 as the mode information. In the present embodiment, "0" denotes "angle knob mode," and "1" denotes "game mode."

As illustrated in FIGS. 23 and 24, mode information 80a from the identification ID 80 is outputted to the scaling correction portion 47 of the bending-instruction portion signal-processing portion 31, for example, by communication.

The identification ID 80 is capable of storing or changing various pieces of information by communication using the identification ID output device (not shown) or the communication portion 34 with the control unit 3 through the PC 10.

The scaling correction portion 47 operates similarly to that in the first embodiment. At the time of the scaling correction, the scaling correction portion 47 operates such that the sign of the correction multiplying value Z in the UP and the DOWN direction is changed over to a plus or a minus according to the mode information 80a of the identification ID 80.

In this case, if the manual input position of the joystick 9A being a bending instruction portion lies, for example, in the position illustrated in FIG. 25, the scaling correction portion 47 determines the operation mode based on the mode information 80a from the identification ID 80.

For example, if the scaling correction portion 47 determines that the mode information 80a is "0," the scaling correction portion 47 recognizes "0" as "angle knob mode," changes over the sign of the correction multiplying value Z to a minus and performs the scaling correction. This sets the angle knob mode, so that the bending instruction portion operation-signal with the output range 70B in which the input position in FIG. 25 is inverted as illustrated in the electric signal coordinate diagram in FIG. 27 can be obtained after the scaling correction.

On the other hand, if the scaling correction portion 47 determines that the mode information 80a is "1," the scaling correction portion 47 recognizes "1" as "game mode," changes over the sign of the correction multiplying value Z to a plus and performs the scaling correction. This sets the game mode, so that the bending instruction portion operation-signal with the output range 70A corresponding to the input position in FIG. 25 as illustrated in the electric signal coordinate diagram in FIG. 26 can be obtained after the scaling correction.

Other configuration and effects are the same as those of the first embodiment.

According to the second embodiment, it is capable of producing the same effect as that of the first embodiment and setting "angle knob mode" or "game mode" according to the mode information 80a from the identification ID 80, so that the second embodiment substantially contributes to improvement in user friendliness.

Third Embodiment

Figure 28:
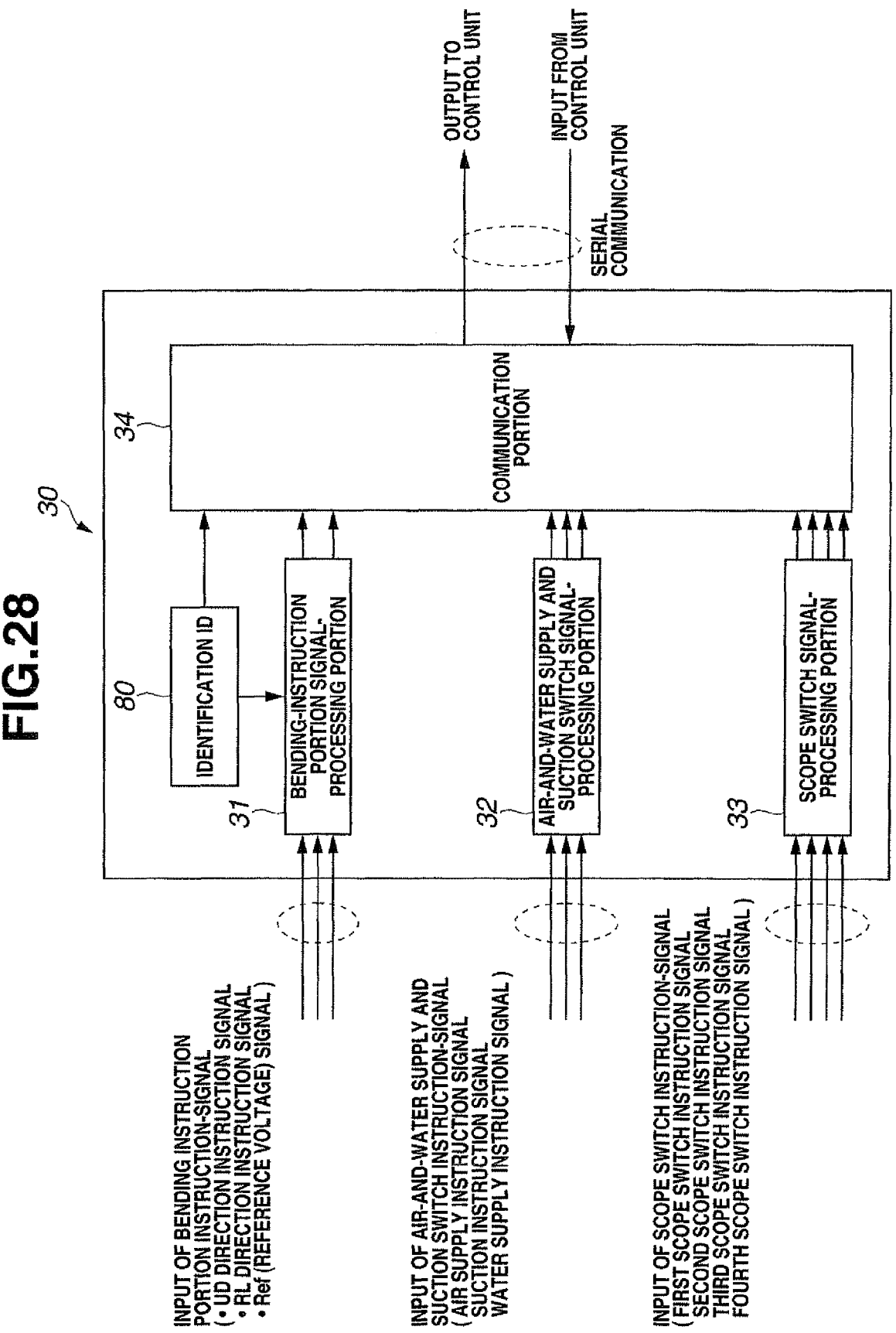
FIG. 28 is a block diagram illustrating the configuration of a control portion provided in the operation portion of the electric bending endoscope device according to a third embodiment of the present invention.
Figure 29:
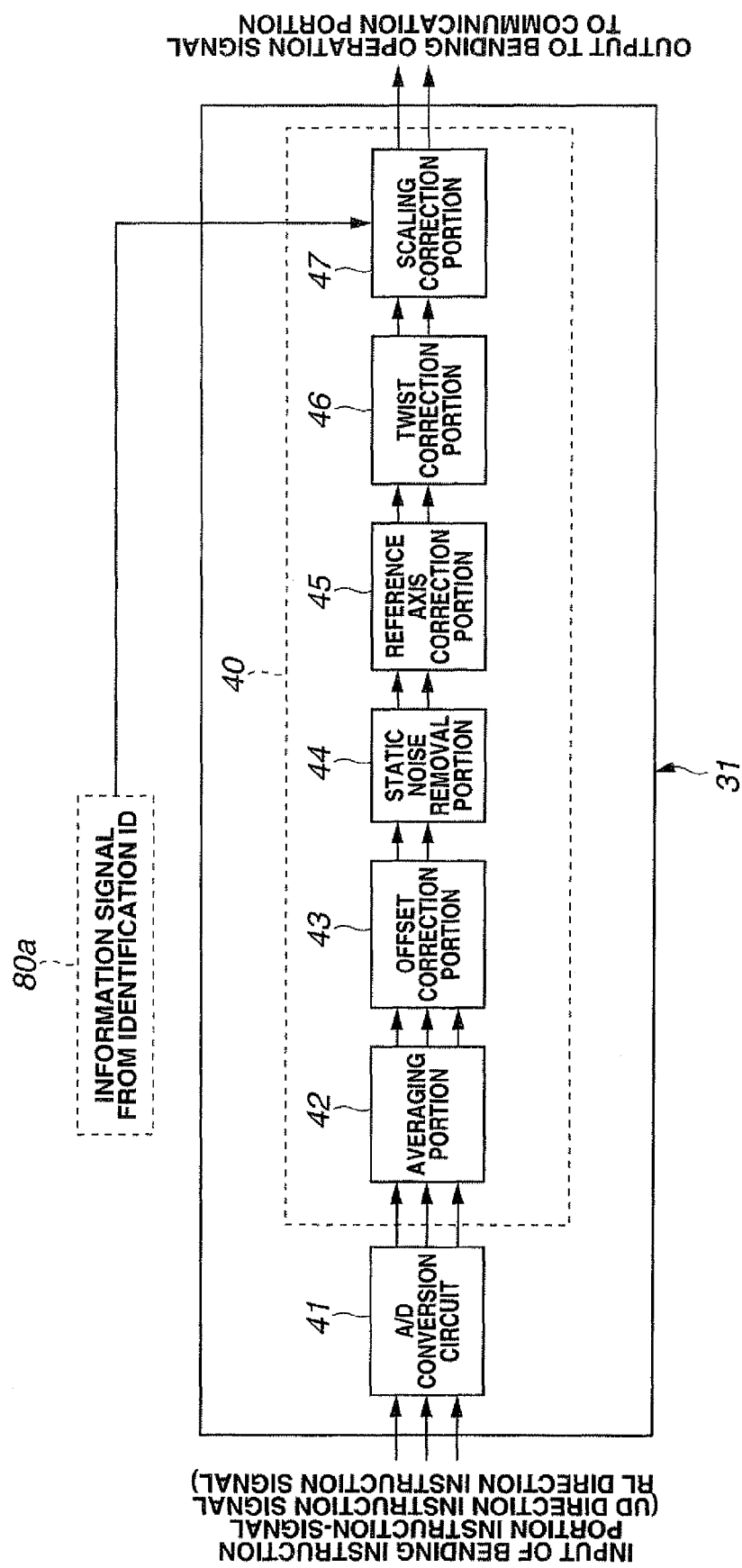
FIG. 29 is a block diagram illustrating a concrete configuration of the signal processing portion in the bending instruction portion in FIG. 28.

FIGS. 28 and 29 relate to the third embodiment of the electric bending endoscope device of the present invention. FIG. 28 is a block diagram illustrating the configuration of the control portion provided in the operation portion. FIG. 29 is a block diagram illustrating a concrete configuration of the bending instruction portion signal-processing portion in FIG. 28. In FIGS. 28 and 29, the composing elements, which are the same as those of the second embodiment, are given the same reference numerals and characters to omit the description thereof. Only portions different from those of the second embodiment are described.

In the present embodiment, as illustrated in FIG. 28, a reference voltage signal (also referred to as Ref voltage signal) is inputted from the bending instruction portion 9A to the bending-instruction portion signal-processing portion 31.

That is to say, as illustrated in FIG. 29, the Ref voltage signal is inputted to the A/D conversion circuit 41 of the bending-instruction portion signal-processing portion 31. The Ref voltage signal is converted to a digital signal by the A/D conversion circuit 41, thereafter, the averaging portion 42 removes noise components from the digital signal as is the case with the first embodiment and outputs it to the offset correction portion 43 at the rear stage.

In the first embodiment, the offset correction portion 43 subjects the inputted bending instruction portion instruction-signal to the correction process (or, the offset correction) in which the individual difference "b" is matched using a reference value stored in a storing portion (not shown). In the present embodiment, however, the offset correction is performed using the supplied Ref voltage signal.

Specifically, for example, if the UP and the DOWN instruction signal voltage (or, UD voltages) are taken as VUD and the Ref voltage signal voltage taken as VRef, the calculation process of VUD-Vref allows the offset correction process to be performed.

Due to this, the bending instruction portion operation-signal can be subjected to the offset correction process without a storing portion (not shown) for storing the reference value unlike the first embodiment.

The calculation process of VRef-VUD is performed when the mode information 80*a* of the identification ID 80 is "0" (or, the angle knob mode) and the calculation process of VUD-Vref is performed when the mode information 80*a* of the identification ID 80 is "1" (or, the game mode) to enable changing over "angle knob mode" and "game mode" without changing over the sign of the correction multiplying value Z at the time of the scaling correction.

Other configuration and effects are the same as those of the second embodiment.

According to the third embodiment, it is capable of producing the same effect as that of the second embodiment. Furthermore, the input of the Ref voltage signal enables the offset correction to be performed without using the reference value stored in the storing portion (not shown), so that the removal of the storing portion (not shown) in the offset correction portion 43 allows cost reduction.

Although the process is described above in which the instruction state of the input portion is converted to an operation signal when an operator operates the input portion such as a joystick, the application of the configuration is not limited to an electric endoscope and it is needless to say that the configuration is applicable to an apparatus which operates an actuator with at least one degree of freedom.

The present invention is not limited to the above first to third embodiments, but may be variously modified and executed without departing from the gist of the present invention.

What is claimed is:

1. An electric bending endoscope device comprising:
   an endoscope having a bending portion in its insertion portion to be inserted to a test subject;
   a drive portion for bending the bending portion;
   an operation portion having a bending instruction portion attached to the operation portion, the bending instruction portion outputting an instruction signal for instructing the bending movement by inputting instructions of bending movements to the endoscope, generating an operation signal based on the instruction signal from the bending instruction portion and outputting the operation signal; and
   a control unit for controlling the drive portion based on the operation signal from the operation portion; wherein
   the operation portion is configured to convert, in a correction algorithm portion, the output range of the instruction signal of the bending instruction portion to cause the output range of the instruction signal of the bending instruction portion to coincide with a predetermined output range of the operation signal outputted by the operation portion according to the bending instruction portion and to generate the operation signal, and wherein
   the correction algorithm portion includes:
   a reference axis correction portion which subjects the instruction signal to a correction process so that the direction from the reference position in the instruction range of the bending instruction portion to an instruction input position coincides with a predetermined bending direction of the bending portion;
   a twist correction portion which performs correction so that the shape of the output range of the output signal of the reference axis correction portion is made similar to a predetermined shape of the bending range of the bending portion; and
   a scaling correction portion for performing a scaling correction in which the instruction signal is multiplied by a set correction multiplying value so that the output range of the instruction signal according to the instruction range of the bending instruction portion is caused to coincide with the maximum movable range of the bending portion, the scaling correction portion changing over the sign of the correction multiplying value in the upper and the lower direction of the bending portion to a plus or a minus according to information from an identification ID provided on the operation portion.

2. The electric bending endoscope device according to claim 1, wherein
   the endoscope is an electric bending endoscope and
   a holding portion of the electric bending endoscope is provided with the drive portion.

3. The electric bending endoscope device according to claim 1, wherein the bending instruction portion is a joystick.

4. The electric bending endoscope device according to claim 2, wherein the bending instruction portion is a joystick.

\* \* \* \* \*